(12) United States Patent
Taylor et al.

(10) Patent No.: US 11,504,075 B2
(45) Date of Patent: Nov. 22, 2022

(54) SYSTEM, METHODS, AND DEVICES FOR CALCULATING HYPOXIC FRACTION AND EQUILIBRATION RATE OF SMALL MOLECULAR WEIGHT TRACERS USING DYNAMIC IMAGING

(71) Applicant: UNIVERSITY HEALTH NETWORK, Toronto (CA)

(72) Inventors: Edward Taylor, Toronto (CA); David A. Jaffray, Etobicoke (CA); Ivan Wai Tong Yeung, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 966 days.

(21) Appl. No.: 16/227,845

(22) Filed: Dec. 20, 2018

(65) Prior Publication Data
US 2019/0183437 A1     Jun. 20, 2019

Related U.S. Application Data

(60) Provisional application No. 62/608,416, filed on Dec. 20, 2017.

(51) Int. Cl.
*A61B 6/00*     (2006.01)
*A61B 6/03*     (2006.01)
(Continued)

(52) U.S. Cl.
CPC .............. *A61B 6/037* (2013.01); *A61B 5/055* (2013.01); *A61B 6/463* (2013.01); *A61B 6/481* (2013.01);
(Continued)

(58) Field of Classification Search
CPC ..... A61B 2576/00; A61B 5/055; A61B 6/037; A61B 6/463; A61B 6/481; A61B 6/507;
(Continued)

(56) References Cited

U.S. PATENT DOCUMENTS

2014/0285198 A1\* 9/2014 Halpern ................. G01V 3/104
324/322
2016/0296538 A1\* 10/2016 Hart ..................... A61K 31/675

OTHER PUBLICATIONS

Fleming, IN et al., Imaging tumour hypoxia with positron emission tomography, Brit J Cancer, 2015, 112, 238-250.
(Continued)

*Primary Examiner* — Mark D Remaly
(74) *Attorney, Agent, or Firm* — Norton Rose Fulbright Canada LLP

(57) ABSTRACT

Uptake of hypoxia-sensitive PET tracers is dependent on tissue transport properties, specifically, distribution volume. Variability in tissue transport properties reduces the sensitivity of static PET imaging to hypoxia. When tissue transport ($v_d$) effects are substantial, correlations between the two methods of determining hypoxic fractions are greatly reduced—that is, trapping rates $k_3$ are only modestly correlated with tumour-to-blood ratio (TBR). In other words, the usefulness of dynamic- and static-PET based hypoxia surrogates, trapping rate $k_3$ and TBR, in determining hypoxic fractions is reduced in regions where diffusive equilibrium is achieved slowly. A process is provided for quantifying hypoxic fractions using a novel biomarker for hypoxia, hypoxia-sensitive tracer binding rate $k_b$, based on PET imaging data. The same formalism can be applied to model the kinetics of non-binding CT and MT contrast agents, giving histopathological information about the imaged tissue.

11 Claims, 24 Drawing Sheets

(51) Int. Cl.
| | |
|---|---|
| G16H 30/40 | (2018.01) |
| A61B 5/055 | (2006.01) |
| A61K 49/00 | (2006.01) |
| G01T 1/161 | (2006.01) |
| G06T 7/00 | (2017.01) |
| A61K 51/04 | (2006.01) |
| G06T 11/00 | (2006.01) |
| G01T 1/29 | (2006.01) |

(52) U.S. Cl.
CPC ............ *A61B 6/507* (2013.01); *A61B 6/5235* (2013.01); *A61K 49/0002* (2013.01); *A61K 51/0491* (2013.01); *G01T 1/1611* (2013.01); *G06T 7/0012* (2013.01); *G06T 11/008* (2013.01); *G16H 30/40* (2018.01); *A61B 2576/00* (2013.01); *G01T 1/2985* (2013.01); *G06T 2207/30096* (2013.01)

(58) Field of Classification Search
CPC .............. A61B 6/5235; A61K 49/0002; A61K 51/0491; G01T 1/1611; G01T 1/2985; G06T 11/008; G06T 2207/30096; G06T 7/0012; G16H 30/40; G16H 40/63; G16H 50/50; G16H 80/00
See application file for complete search history.

(56) References Cited

OTHER PUBLICATIONS

Rajendran, JG et al., F-18 fluoromisonidazole for imaging tumor hypoxia: imaging the microenvironment for personalized cancer therapy, Semin Nucl Med, 2015, 45(2), 151-162.
Koh, WJ et al., Imaging of hypoxia in human tumors with [F-18]fluoromisonidazole, Int J Radiat Oncol Biol Phys, 1992, 22(2), 199-212.
Rajendran, JG et al., Tumor hypoxia imaging with [F-18] fluoromisonidazole positron emission tomography in head and neck cancer, Clin Cancer Res, Sep. 15, 2006, 12(18), 5435-5441.
Muzi, M et al., 18F-Fluoromisonidazole Quantification of Hypoxia in Human Cancer Patients Using Image-Derived Blood Surrogate Tissue Reference Regions, J Nucl Med, 2015, 56(8), 1223-1228.
Pruijn, FB et al., Prediction of tumour tissue diffusion coefficients of hypoxia-activated prodrugs from hysicochemical parameters, Aust. J. Chem, 2008, 61, 687-693.
Wack, LJ et al., Comparison of [18F]-FMISO, [18F]-FAZA, and [18F]-HX4 for PET imaging of hypoxia—a simulation study, Acta Oncologica, 2015, 54, 1370-1377.
Lau, SK et al., Differential expression of MUC1, MUC2, and MUC5AC in carcinomas of various sites: an immunohistochemical study, Am J Clin Pathol, Jul. 2004, 122(1), 61-69.
Kaur, S et al., Mucins in pancreatic cancer and its microenvironment, Nat Rev Gastroenterol Hepatol, Oct. 2013, 10(10), 607-620.
Georgiades, P et al., Particle tracking microrheology of purified gastrointestinal mucins, Biopolymers, 2013,101(4), 366-377.
Runnsjo, A et al., Diffusion through Pig Gastric Mucin: Effect of Relative Humidity, PLoS One, Jun. 23, 2016, 11(6), e0157596.
Casciari, JJ et al., A modeling approach for quantifying tumor hypoxia with [F-18]fluoromisonidazole PET time-activity data, Med. Phys, 1995, 22, 1127-1139.
Thorwarth, D et al., A kinetic model for dynamic [18F]-Fmiso PET data to analyse tumour hypoxia, Phys Med Biol, 2005, 50, 2209-2224.
Thorwarth, D et al., Kinetic analysis of dynamic 18F-fluoromisonidazole PET correlates with radiation treatment outcome in head-and-neck cancer, BMC Cancer, Dec. 1, 2005, 5, 152.
Wang W et al., Evaluation of a compartmental model for estimating tumor hypoxia via FMISO dynamic PET imaging, Phys Med Biol, 2009, 54, 3083-3099.
Metran-Nascente C et al., Measurement of tumor hypoxia in patients with advanced pancreatic cancer based on 18F-fluoroazomyin arabinoside uptake, J Nucl Med, 2016, 57(3), 361-366.
Wang, W et al., Pharmacokinetic Analysis of Hypoxia 18F-Fluoromisonidazole Dynamic PET in Head and Neck Cancer, J Nucl Med, 2010, 51(1), 37-45.
Bartlett, RM et al., Image-Guided PO2 Probe Measurements Correlated with Parametric Images Derived from 18F-Fluoromisonidazole Small-Animal PET Data in Rats, J Nucl Med, 2012, 53(10), 1608-1615.
Wang, K et al., Hypoxia Imaging of Rodent Xenografts with 18F-Fluoromisonidazole: Comparison of Dynamic and Static PET Imaging, Int J Med Physics, Clin Eng and Radiation Oncology, 2012, 1(3), 95-104.
Patlak, CS et al., Graphical evaluation of blood-to-brain transfer constants from multiple-time uptake data, J Cereb Blood Flow Metab, Mar. 1983, 3(1), 1-7.
Taylor, E et al., Quantifying hypoxia in human cancers using static PET imaging, Phys. Med. Biol, 2016, 61, 7957-7974.
Larson, KB et al., Tracer-kinetic models for measuring cerebral blood flow using externally detected radiotracers, J Cereb Blood Flow Metab, 1987, 7(4), 443-463.
Nordsmark, M et al., Measurement of human tumour oxygenation status by a polarographic needle electrode. An analysis of inter- and intratumour heterogeneity, Acta Oncol, 1994, 33(4), 383-389.
Lorenz, CD et al., Precise determination of the critical percolation threshold for the three-dimensional "Swiss cheese" model using a growth algorithm, J Chem Phys, 2001, 114(8), 3659-3661.
Grkovski, M et al., Multiparametric Imaging of Tumor Hypoxia and Perfusion with 18F-Fluoromisonidazole Dynamic PET in Head and Neck Cancer, J Nucl Med, 2017, 58, 1072-1080.
Busk, M et al., Resolution in PET hypoxia imaging: Voxel size matters, Acta Oncologica, 2008, 47(7), 1201-1210.
Freedman, NM et al., Comparison of SUV and Patlak slope for monitoring of cancer therapy using serial PET scans, Eur J Nucl Med Mol Imaging, Jan. 2003, 30(1), 46-53.
Doot, RK et al., Dynamic and static approaches to quantifying 18F-FDG uptake for measuring cancer response to therapy, including the effect of granulocyte CSF, J Nucl Med, Jun. 2007, 48(6), 920-925.
Grkovski, M et al., Monitoring early response to chemoradiotherapy with 18F-FMISO dynamic PET in head and neck cancer, Eur J Nucl Med Mol Imaging, Sep. 2017, 44(10), 1682-1691.
Takikita, M et al., Associations between Selected Biomarkers and Prognosis in a Population-Based Pancreatic Cancer Tissue Microarray, Cancer Res, Apr. 2009, 69(7), 2950-2955.
Yamazoe, S et al., RNA interference suppression of mucin 5AC (MUC5AC) reduces the adhesive and invasive capacity of human pancreatic cancer cells, J Exp Clin Cancer Res, May 23, 2010, 29, 53.
Hoshi, H et al., Tumor-associated MUC5AC stimulates in vivo tumorigenicity of human pancreatic cancer, Int J Oncol, Mar. 2011, 38(3), 619-627.
Busk, M et al., Assessing hypoxia in animal tumor models based on pharmacokinetic analysis of dynamic FAZA PET, Acta Oncol, Oct. 2010, 49(7), 922-933.

\* cited by examiner

Table 2: Correlation matrix of Pearson correlation co-efficients between the tumour-scale parameters across the twenty tumours studied using the two-hour data sets.

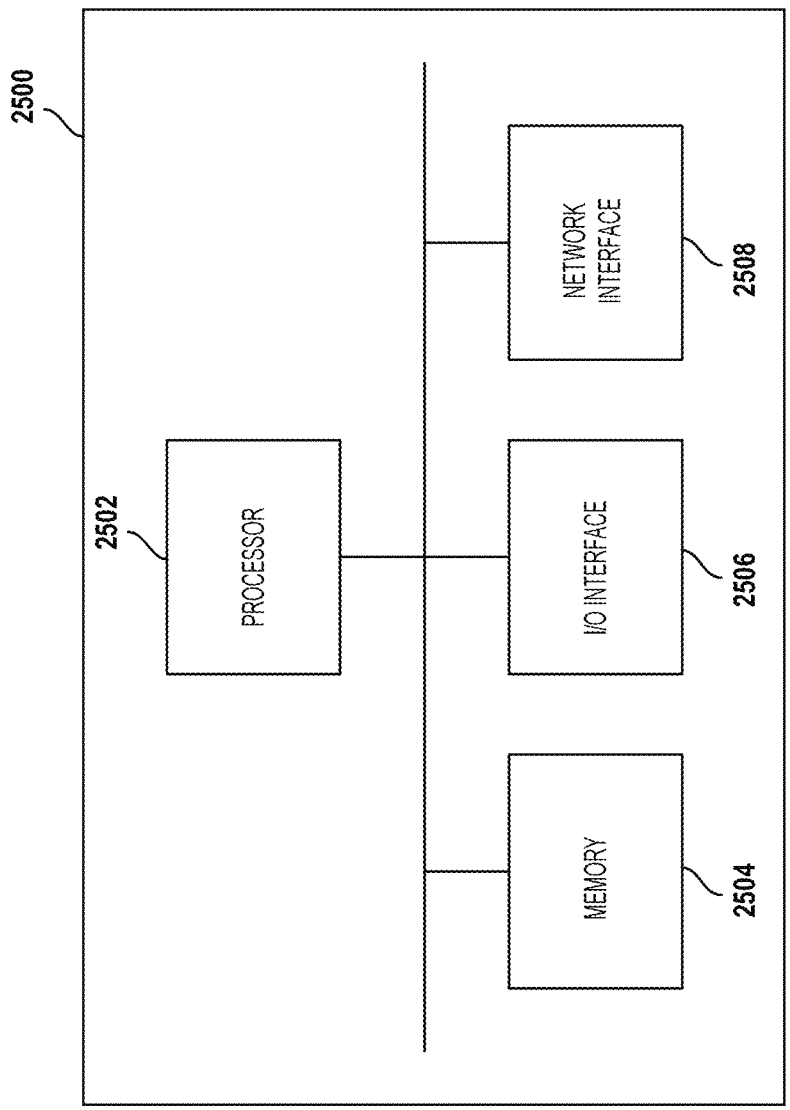

SYSTEM, METHODS, AND DEVICES FOR CALCULATING HYPOXIC FRACTION AND EQUILIBRATION RATE OF SMALL MOLECULAR WEIGHT TRACERS USING DYNAMIC IMAGING

CROSS-REFERENCE TO RELATED APPLICATIONS

This application claims all benefit including priority to U.S. Provisional Patent Application 62/608,416, filed Dec. 20, 2017, and entitled: "System, Methods, and Devices for Calculating Hypoxic Fraction using Dynamic PET Imaging", which is hereby incorporated by reference in its entirety.

FIELD

Embodiments herein described relate to quantifying hypoxic fractions using positron-emission tomography (PET) imaging and histopathological properties of tissue that determine transport of small molecular-weight contrast agents ("tissue transport properties") using PET, computed tomography (CT) or magnetic resonance (MR) imaging.

INTRODUCTION

The clinical impact of hypoxia in solid tumours is indisputable and yet questions about the sensitivity of hypoxia-PET imaging have impeded its uptake into routine clinical practice. As hypoxia correlates negatively with outcome after surgery and radio- and chemo-therapies, there is a need for an improved process for stratification of patients for hypoxia targeted therapies. Simultaneously, the extent and rate of biodistribution of small-molecular weight imaging agents (PET, MR, and CT) provides additional histopathological information that may enhance the ability to tailor therapies for individuals.

SUMMARY

Embodiments described herein provide a method, device and system for generating output data indicating hypoxic fraction using dynamic PET imaging and, more generally, tissue transport properties using all dynamic imaging modalities, including MR and CT imaging.

Embodiments described herein provide a platform, device and process for quantifying hypoxic fractions based on a hypoxia biomarker generated using PET imaging data. In particular, embodiments described herein can provide a platform, device and process for generating a two-tissue compartment model and data indications representing values for a hypoxia biomarker, hypoxia-sensitive binding rate $k_b$, based on PET imaging data. The same model can be applied to quantify the tissue transport kinetics of non-binding MR and CT contrast agents.

Embodiments described herein provide a process for quantifying hypoxic fractions using a novel biomarker for hypoxia, hypoxia-sensitive tracer binding rate $k_b$, based on PET imaging data, as well as the equilibration rate of non-binding MR and CT contrast agents, a biomarker that will provide additional histopathological information of imaged tissues.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

DESCRIPTION OF THE FIGURES

In the figures, embodiments are illustrated by way of example. It is to be expressly understood that the description and figures are only for the purpose of illustration and as an aid to understanding.

In the figures which depict example embodiments:

FIG. 24 depicts a schematic diagram of a computing device such as a server.

DETAILED DESCRIPTION

Figure 1:
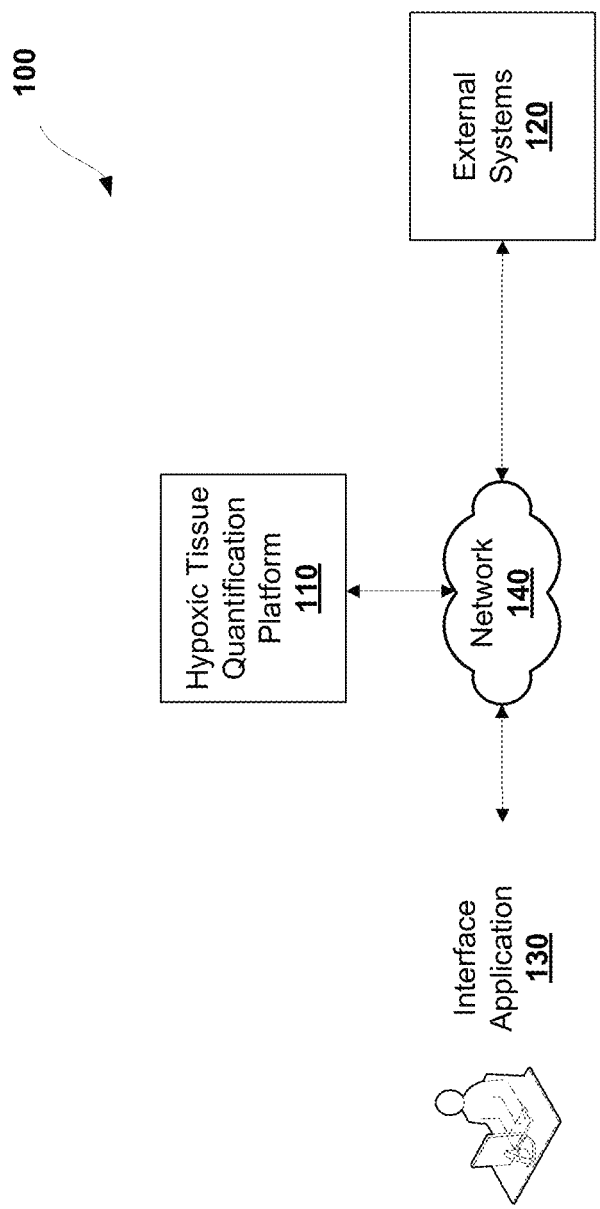
FIG. 1 is a view of an example hypoxic tissue quantification system, including a hypoxic tissue quantification platform.

The clinical impact of hypoxia in solid tumours is indisputable and yet questions about the sensitivity of hypoxia-PET imaging have impeded its uptake into routine clinical practice. Notably, the binding rate of small-molecular weight tracers such as those (FAZA) used for PET quantification of hypoxia is slow, comparable to the rate of diffusive equilibration in some tissue types, including mucinous and necrotic tissue. This means that tracer uptake on the scale of a PET imaging voxel—large enough to include such tissue and hypoxic cells—can be as much determined by tissue transport properties as it is by hypoxia. At the same time, there is considerable value in the quantification of these transport properties, as they give further information into the histopathological properties of the tissue.

In an example experiment, dynamic PET imaging of twenty patients with pancreatic ductal adenocarcinoma was used to assess the impact of transport on surrogate metrics of hypoxia: the tumour-to-blood ratio (TBR) and the trapping rate $k_3$ inferred from a two-tissue compartment model. Transport quantities obtained from this model included the vascular influx and efflux rate coefficients, $k_1$ and $k_2$, and the distribution volume $v_d \equiv k_1/(k_2+k_3)$. Correlations between voxel- and whole tumour-scale $k_3$ and TBR values were weak to modest: the population average of the Pearson correlation coefficients (r) between voxel-scale $k_3$ and TBR (1 hr) [TBR(2 hrs)] values was 0.10 [0.01] in the twenty patients, while the correlation between tumour-scale $k_3$ and TBR(2 hrs) values was 0.58. Using Patlak's formula to correct uptake for the distribution volume, correlations became strong (r=0.80[0.52] and r=0.93, respectively). The distribution volume was substantially below unity for a large fraction of tumours studied, with $v_d$ ranging from 0.68 to 1 (population average, 0.85). Surprisingly, $k_3$ values were strongly correlated with $v_d$ in all patients. A model was used to explain this in which $k_3$ is a combination of the hypoxia-sensitive tracer binding rate $k_b$ and the rate $k_{eq}$ of equilibration in slow-equilibrating regions occupying a volume fraction $1-v_d$ of the imaged tissue. This model was used to determine the proposed hypoxia surrogate marker $k_b$. The same equilibration processes are also manifested in the kinetics of non-binding small molecular-weight tracers commonly used in dynamic contrast imaging (e.g., Gadolinium- and Iodine-based MR and CT contrast agents, respectively) and this model can be applied to those imaging modalities to provide novel histopathological information through $k_{eq}$ and $v_d$. Therefore, although the description below is provided with references to the model as applied for hypoxia, the teachings in the description can also be modified and applied with respect to the determination of equilibration of MR and CT contrast agents.

Small molecular-weight imaging tracers are slow to reach diffusive equilibrium in a substantial fraction of pancreatic tumours and other hypo-perfused or mucinous tissue, confounding quantification of hypoxia using both static (TBR) and dynamic ($k_3$) PET imaging. TBR is reduced by distribution volume effects and $k_3$ is enhanced by slow equilibration. A novel model can be used to quantify tissue transport properties and hypoxia-sensitive tracer binding in order to improve the sensitivity of hypoxia-PET imaging and to quantify regions of a given histopathology in which equilibration is slow.

Uptake of hypoxia-sensitive PET tracers is dependent on tissue transport properties, specifically, distribution volume. Variability in tissue transport properties reduces the sensitivity of static PET imaging to hypoxia. When tissue transport ($v_d$) effects are substantial, correlations between the two methods of determining hypoxic fractions are greatly reduced—that is, trapping rates $k_3$ are only modestly correlated with tumour-to-blood ratio (TBR). In other words, the usefulness of dynamic- and static-PET based hypoxia surrogates, trapping rate $k_3$ and TBR, in determining hypoxic fractions is reduced in regions where diffusive equilibrium is achieved slowly.

Embodiments described herein provide a platform, device, and process for quantifying hypoxic fractions using a novel biomarker for hypoxia, hypoxia-sensitive tracer binding rate $k_b$, based on PET imaging data. This can enable reliable stratification of patients for hypoxia-targeted therapies. One example of the value in stratification is due to how hypoxia correlates negatively with outcome after surgery and radio- and chemo-therapies. Embodiments described herein can allow prediction of the prognostic suitability of patients for hypoxia-targeted therapies based on PET scans and, in turn, save lives.

It should be understood that the embodiments described herein with reference to the hypoxic tissue quantification system 100 and platform 110 may also apply to a more general tissue quantification system and platform applicable to other small molecular weight agents such as CT and MR contrast agents, with respect to their equilibration properties.

Embodiments described herein provide a platform, device and process for quantifying hypoxic fractions based on a novel hypoxia biomarker using PET imaging data. In particular, embodiments described herein provides a platform, device and process for generating a two-tissue compartment model and data indications representing values for a novel hypoxia biomarker, hypoxia-sensitive binding rate $k_b$, based on PET imaging data.

FIG. 1 is a view of an example hypoxic tissue quantification system 100 according to some embodiments. Hypoxic tissue quantification system 100 includes hypoxic tissue quantification platform 110, interface application 130, one or more external systems 120, and network 140 (or multiple networks). The hypoxic tissue quantification system 100 includes a memory and a processor configured as described herein.

Hypoxic tissue quantification platform 110 connects to interface application 130, for example, to receive imaging data, such as PET scans, computed tomography (CT) scans, and/or other medical imaging data on one or more of a variety of tissue types. Hypoxic tissue quantification platform 110 may receive other data from interface application 130, such as, data representing modification to imaging data, input from a user or physician engaged at interface application 130, and computational models for processing, transforming, or generating data, for example, improving accuracy, speed, or transmission of data received for generated by hypoxic tissue quantification platform 110.

Hypoxic tissue quantification platform 110 is configured to process, organize the received data and/or aggregate the received data with other data using image identification data, patient identification data, time stamps, and/or clock data for synchronization. For example, platform 110 is configured to co-register CT images to PET images, contour regions of interest based on slices from one or more PET scans and CT scans, and generate PET activity data for regions of interest contoured using co-registered CT images. Platform 110 is configured to receive data corresponding to each of these stages, for example, data representing regions of interest contoured using co-registered CT images.

Interface application 130 is configured to engage a user to receive data input and/or to receive imaging data, such as PET scans, CT scans, and/or other medical imaging data on one or more of a variety of tissue types from one or more external systems 120, such as a PET scanner, CT scanner, PET-CT scanner, or computer receiving data from same.

In some embodiments, interface application 130 is configured to engage a user, for example, via a display, interactive display, keyboard, mouse, or other sensory apparatus. Interface application 130 is configured to transmit and receive signals or data from such devices and cause data to be transmitted to hypoxic tissue quantification platform 110.

In some embodiments, interface application 130 is configured to process data before transmitting the data via network 140 and/or to hypoxic tissue quantification platform 110.

Hypoxic tissue quantification platform 110 is configured to connect to interface application 130 via a network 140 (or multiple networks). Network 140 (or multiple networks) is capable of carrying data and can involve wired connections, wireless connections, or a combination thereof. Network 140 may involve different network communication technologies, standards and protocols, for example.

In some embodiments, external system 120 is configured to connect to hypoxic tissue quantification platform 110 and/or interface application 130, for example, via network 140 (or multiple networks). External systems 120 can be one or more databases, data sources, or one or more entities that aggregate, process, or provide data. For example, an external system 120 can be a system including a PET or CT scanner or one or more data stores encoding patient, image, tissue, and/or computational modeling data. External system 120 may be configured to provide a compartmental model to a first hypoxic tissue quantification platform 110 where the model is generated by a second hypoxic tissue quantification platform 110, for example. The first hypoxic quantification platform 110 may store or use the compartmental model to generate one or more voxel- or whole tumour-scale values (e.g., $k_3$, $v_d$, TBR, $TBR_{corrected}$) or hypoxia biomarker $k_b$ values, for example. This connectivity can improve the efficiency with which a hypoxic tissue quantification platform 110 may generate hypoxia biomarker $k_b$ values or generate pharmacokinetic data from PET activity data, for example.

In some embodiments, external system 120 is configured to receive data from an interface application 130 and/or hypoxic tissue quantification platform 110. This connectivity can facilitate the viewing, manipulation, and/or analysis of the data by a researcher, developer, and/or healthcare provider engaged with an external system 150, for example.

Figure 2:
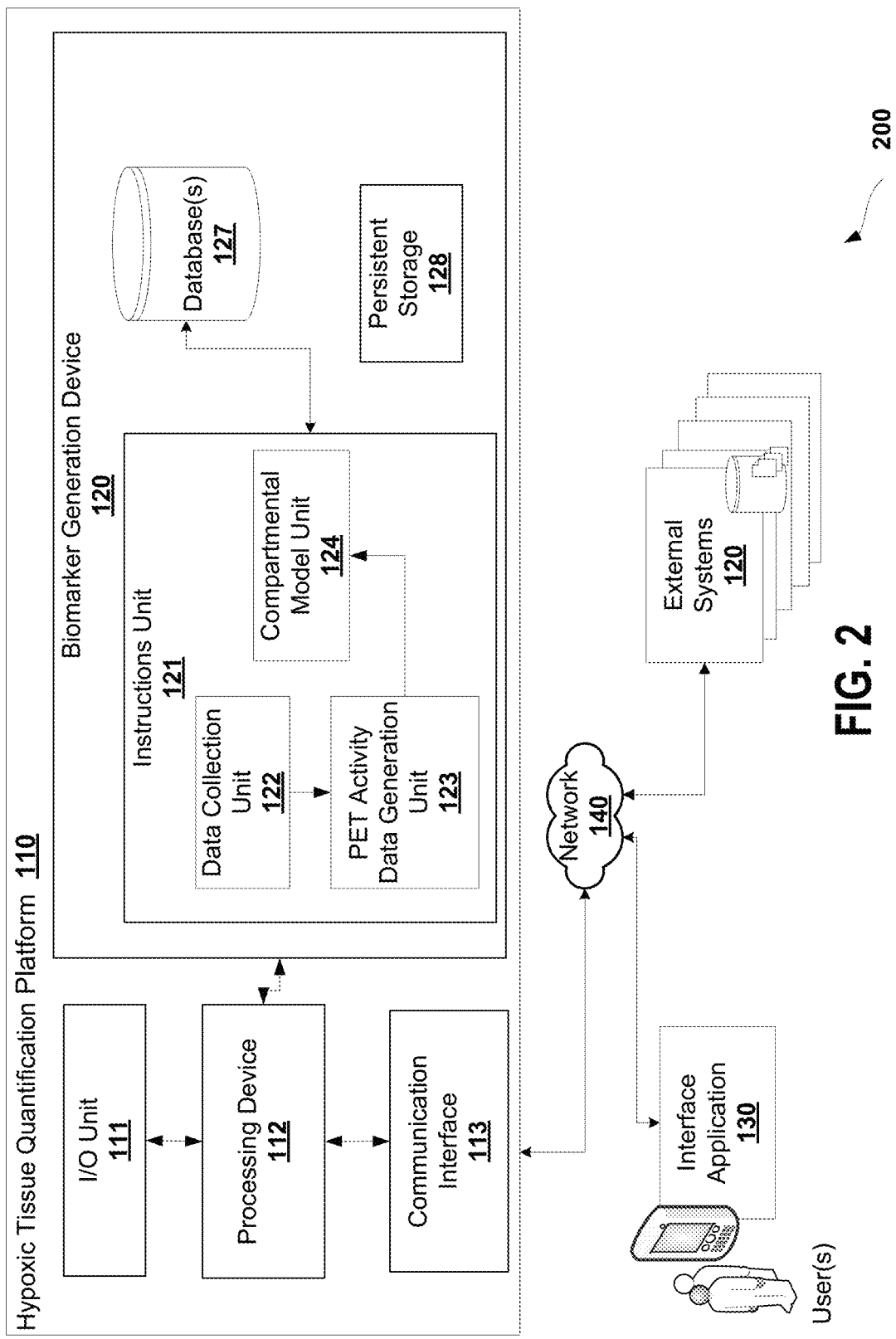
FIG. 2 is a view of an example hypoxic tissue quantification platform of FIG. 1.

FIG. 2 is a view of an example hypoxic tissue quantification platform 110 according to some embodiments. A hypoxic tissue quantification platform 110 can include an I/O Unit 111, processing device 112, communication interface 113, and biomarker generation device 120.

The hypoxic tissue quantification platform 110 is configured to connect with one or more interface applications 130 and/or external systems 120. This connection may be over a network 140 (or multiple networks). Hypoxic tissue quantification platform 110 receives and transmits data from one or more of these via I/O unit 111. When data is received, I/O unit 111 transmits the data to processing device 112.

Each I/O unit 111 can enable the hypoxic tissue quantification platform 110 to interconnect with one or more input devices, such as a keyboard, mouse, camera, touch screen and a microphone, and/or with one or more output devices such as a display screen and a speaker.

A processing device 112 can execute instructions in instructions unit 121 to configure storage device 120, and more particularly, data collection unit 122, PET activity data generation unit 123, and compartmental model unit 124. A processing device 112 can be, for example, a general-purpose microprocessor or microcontroller, a digital signal processing (DSP) processor, an integrated circuit, a field programmable gate array (FPGA), a reconfigurable processor, or combination thereof.

Instructions unit 121 may include a suitable combination of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Biomarker generation device 120 can include instructions unit 121, databases 127, and persistent storage 128.

Each communication interface 113 can enable the hypoxic tissue quantification platform 110 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

The hypoxic tissue quantification platform 110 can be operable to register and authenticate users (using a login, unique identifier, and password for example) prior to providing access to applications, a local network, network resources, other networks and network security devices. The hypoxic tissue quantification 110 may serve one user or multiple users.

The storage 127 may be configured to store information associated with or created by the biomarker generation device 120. Storage 127 and/or persistent storage 128 may be provided using various types of storage technologies, such as solid state drives, hard disk drives, flash memory, and may be stored in various formats, such as relational databases, non-relational databases, flat files, spreadsheets, extended markup files, etc.

In some embodiments, data collection unit 122 is configured to receive data, for example, data representing PET and/or CT scans, slices, frames, images, and/or co-registered images. Data collection unit 122 is configured to process, extract, transform, and/or combine the data, generate new data, and/or store associations between data. This processing can improve scan or image quality, resolution, definition, and/or detail, for example, by selectively combining data from multiple images. For example, data collection unit 122 is configured in some embodiments to use multiple slices or frames taken from a PET scan to generate an improved final image of a tumour or region of interest. Data collection unit 122 can receive data representing regions of interest contoured using co-registered CT images or data representing multiple CT region of interest data sets co-registered to dynamic and static PET scans, for example.

In some embodiments, PET activity data generation unit 123 is configured to generate PET activity data for regions of interest contoured using co-registered CT images, for example, received from data collection unit 122. PET activity data generation unit 123 is configured to extract data from the images or data representing regions of interest and store numerical representations of same in one or more data structures. Storage in the data structures can enable optimal or improved retrieval of the data and/or presentation of the data or transformations of the data, for example, in a graphical form such as a TAC curve for a voxel or whole tumour. For example, the PET activity data can be used by hypoxic tissue quantification platform 110 to generate hypoxia surrogate biomarker $k_b$ values and/or generate a data indication representing a likelihood of hypoxia or quantification of a hypoxic fraction in tissue. It should be understood that PET Activity Data Generation Unit 123 may be replaced with a general imaging concentration data generation unit to generate CT or MR concentration data for the regions of interest.

In some embodiments, compartmental model unit 124 is configured to generate a compartmental model, for example, a two-tissue compartment model that relates $k_3$ (trapping rate) to $k_b$ (hypoxia-sensitive tracer binding rate) and $k_{eq}$, where $k_{eq}$ is the equilibration rate in slow equilibrating regions occupying a volume fraction $1-v_d$ of imaged tissue and $v_d$ is the distribution volume. Compartmental model unit 124 is configured to generate partition coefficients ($v_d$) and other pharmacokinetic values based on PET activity data received from PET activity data generation unit 123, for example. For example, compartmental model unit 124 can receive dynamic PET activity data for one or more regions of interest, generate data values encoding data points fitted to dynamic PET time activity curves (TACs), and generate data representations of various relationships between various features of the PET activity data. Compartmental model unit 124 can fit the generated two-tissue compartment model to TACs generated for each voxel, whole tumour, and/or region of interest to generate the relationships and the features. This can enable generation of hypoxia surrogate biomarker $k_b$ values and/or generate a data indication representing a likelihood of hypoxia or quantification of a hypoxic fraction in tissue, where the tissue is represented by a plurality of voxels by hypoxic tissue quantification platform 110. It should be understood that for non-binding CT and MR tracers, the quantification platform would be applicable with $k_b=0$.

Hypoxic tissue quantification platform 110 is configured to store (e.g., in databases 127, persistent storage 128) and/or transmit (e.g., to external systems 120 or interface application 130) data, for example, encoding a generated two-tissue compartment model, results generated from a model and based on PET activity data, indications representing a likelihood of hypoxia or quantification of a hypoxic fraction in tissue, and/or hypoxia surrogate biomarker kb values in relation to a specified (or group of) scan, image, slice, tissue, region of interest, patient, tumour, or other data received by hypoxic tissue quantification platform 110.

Figure 3:
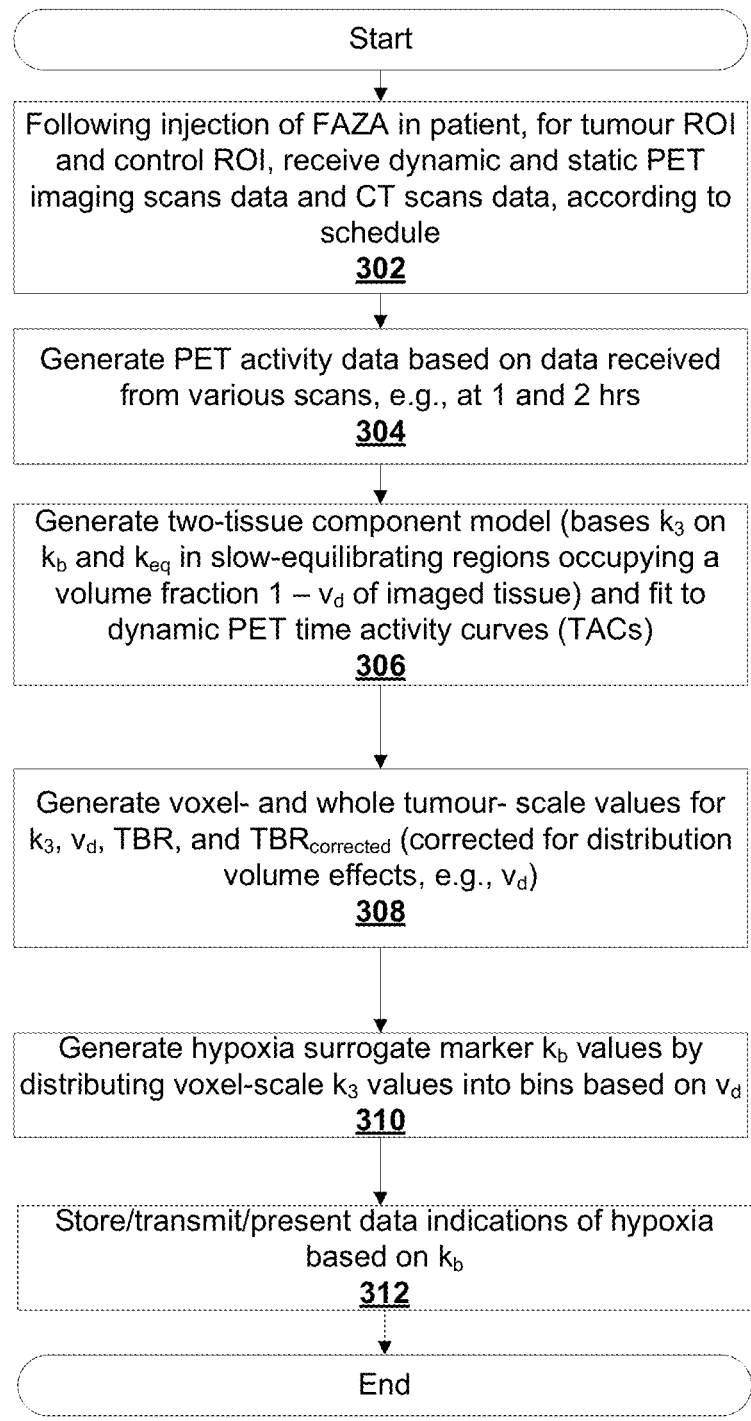
FIG. 3 is a flow diagram of an example process for generating data indications of hypoxia based on $k_b$.

FIG. 3 is a flow diagram of an example process for generating data indications of hypoxia based on $k_b$, according to some embodiments. Steps 302 to 306 may be modified to apply to non-binding small molecular weights agents (without the need for steps 308 to 312).

At 302, following injection of FAZA in a patient, for each of tumour ROI and control ROI, hypoxic tissue quantification platform 110 is configured to receive dynamic and static PET imaging scans data and CT scans data, according to a schedule. For the non-binding small molecular weight embodiment, following injection of CT and MR agents in a patient, for each of tumour ROI, a tissue quantification platform may be configured to receive dynamic CT and MR imaging data, according to a schedule.

At 304, hypoxic tissue quantification platform 110 is configured to generate PET activity data based on data received from various scans, e.g., at 1 and 2 hrs following injection of FAZA. For the non-binding small molecular weight embodiment, a tissue quantification platform may be configured to generate MR or CT time concentration data based on data received from various scan, e.g., at 5 minutes following injection of MR or CT agents.

At 306, hypoxic tissue quantification platform 110 is configured to generate a two-tissue compartment model (which bases $k_3$ on $k_b$ and $k_{eq}$, where $k_{eq}$ is the equilibration rate in slow-equilibrating regions occupying a volume fraction $1-v_d$ of imaged tissue) and fit the model to dynamic PET time activity curves (TACs), for example voxel- and whole tumour-scale TACs that correspond to received dynamic PET imaging data. For the non-binding small molecular weight embodiment, a tissue quantification platform may be configured to generate a two-tissue compartment model (with $k_b=0$) and fit the model to dynamic MR or CT time concentration curves (TCCs), for example voxel- and whole tumour scale TCCs that correspond to receive dynamic MR and CT imaging data. The method for the non-binding small molecular weight embodiment ends at this step.

At 308, hypoxic tissue quantification platform 110 is configured to generate voxel- and whole tumour-scale values for $k_3$, $v_d$, TBR, and $TBR_{corrected}$ (corrected for distribution volume effects, e.g., $v_d$).

At 310, hypoxic tissue quantification platform 110 is configured to generate hypoxia surrogate marker $k_b$ values by distributing voxel-scale $k_3$ values into bins based on $v_d$.

At 312, hypoxic tissue quantification platform 110 is configured to store, transmit, and/or present data indications of hypoxia based on $k_b$ (binding rate).

The hypoxic tissue quantification system 100 executes computer logic code stored in memory to configure one or more processors to implement the operations described.

PET imaging of hypoxia can detect hypoxia non-invasively in solid tumours. A challenge to this approach is that the binding rate of hypoxia-sensitive PET tracers such as fluoromisonidazole (FMISO) and fluoroazomycinarabinoside (FAZA) is slow as compared to e.g., fluorodeoxyglucose (FDG), and can be comparable to diffusive equilibration rates in tumour tissues.

As an example, a typical threshold used to decide whether or not a PET voxel is hypoxic is that the voxel-scale tracer concentration exceeds that in blood by 20% after two hours; i.e., TBR (2 hrs)>1.2. This means that the binding rate of tracer in hypoxic tissue is $$k_b \gtrsim \frac{0.2}{2 \text{ hrs}} = 0.1 \text{ hrs}^{-1}. \quad (1)$$

In comparison, the rate at which tracer diffuses across a distance l through the extravascular space of tissue scale as is $$k_{eq} \sim d/l^2, \quad (2)$$

where D is the diffusivity of the tracer. For FAZA and similarly sized molecules (on the order of several hundred Daltons), D~10 µm²/s in most tissue. Hence, taking l~100

µm to be the distance between capillaries, the equilibration rate $k_{eq} \sim 20$ hrs$^{-1}$ for tracer is typically much faster than the binding rate, and comparable to the rate of extravasation, $k_1$.

On the other hand, for tissue with substantial mucous deposits (common in carcinomas such as pancreatic ductal adenocarcinoma), where diffusivity can be slowed by two or more orders of magnitude, the rate of equilibration slows drastically, becoming comparable to the binding rate. This can also happen in tissue with necrotic regions (l≥500 µm) interspersed with hypoxic cells.

Slow diffusive equilibration has two important consequences for quantifying tumour hypoxia based on tracer uptake. First, if an imaging voxel contains both hypoxic cells and either mucous or small necroses, the voxel-scale TBR value will be reduced by the fact that tracer does not reach diffusive equilibrium at the standard imaging time, between two and three hours post-injection. Hence, the sensitivity of static PET imaging to hypoxia is diminished. Second, as tracer slowly equilibrates in mucinous and necrotic tissue, its concentration increases at a rate comparable to that due to hypoxia-induced binding and a compartment model may not be able to distinguish the two processes. In this case, the trapping rate $k_3$ may represent a sum of the binding rate $k_b$ and the rate of equilibration. Quantifying hypoxia based on $k_3$ will thus overestimate its extent since $k_3 \geq k_b$.

Example Experiments

Example embodiments can be tested using an example experiment.

In an example experiment, the pharmacokinetics of FAZA in twenty patients with pancreatic ductal adenocarcinoma (PDAC) were modeled, applying principles of diffusive equilibration to interpret transport data calculated from a standard two-tissue compartment model.

Example Methods

Patient Population and PET/CT Scans

Data was taken from twenty patients with biopsy-confirmed pancreatic ductal adenocarcinoma and FAZA-PET scans. Dynamic PET imaging scans were acquired over one hour following injection of FAZA. The one hour time-activity curves (TAC$_1$) were each binned into thirty-four frames: twelve ten-second frames, followed by eight thirty-second frames, followed by seven two-minute frames, followed by seven five-minute frames. Patients returned for a static PET scan at two hours. CT scans used for co-registration were taken at the beginning of the dynamic and static PET scans.

Region of Interest Contours

PET activity data was obtained for regions of interest (ROIs) contoured using co-registered CT images. Tumour ROIs were contoured by a radiologist using the CT scan at two hours. This was co-registered manually to the initial CT scan and the two CT ROI sets were co-registered to the dynamic and static PET scans. In order to minimize effects resulting from high liver uptake of FAZA, aorta ROIs were contoured from the same range of PET/CT slices (along the cranial-caudal axis) as the tumour ROIs. At the level of the pancreas, the aorta is between 1.5 and 2 cm in diameter; to minimize partial volume effects, ROIs in the aorta were restricted to 0.75 cm in diameter and combined so that at least twenty-five PET voxels (3.9×3.9×3.3 mm$^3$ each) were imaged.

Compartment Model Analysis

Dynamic PET TACs of FAZA were analyzed using the two-tissue compartment model:

$$\frac{dC_d(t)}{dt} = k_1 C_{In}(t) - [k_2 + k_3] C_d(t) \text{ and} \qquad (3)$$

$$\frac{dC_b(t)}{dt} = k_3 C_d(t). \qquad (4)$$

Here, the concentration of tracer in the extravascular space of an imaged region has been partitioned into an unbound, diffusing component $C_d$ as well as a component $C_b$ that is bound by hypoxia. $C_{In}$ is the "input" function, which was taken to be the imaged tracer concentration in the aorta, as described above. As noted earlier, $k_1$ and $k_2$ are the vascular influx and efflux coefficients and $k_3$ is the tracer trapping rate. The total tracer concentration in an imaged region is $$C(t) = v_b C_{In}(t) + (1 - v_b)[C_d(t) + C_b(t)], \qquad (5)$$

where $v_b$ is the volume fraction occupied by blood in the region of interest. The above model was fitted to both the one-hour TACs (TAC$_1$) as well as the combined two-hour TAC (TAC$_2$) comprising the one-hour TACs plus static scans at two hours (in part to assess co-registration errors, which should be greater for TAC$_2$). Coefficients ($v_b$, $k_1$, $k_2$, and $k_3$) were determined by minimizing $$X^2 = \sum_i^N w_i [C_{model}(t_i) - C_{data}(t_i)]^2, \qquad (6)$$

where $C_{model}(t_i)$ are the model activity values [Eqs. (3)-(5)] and $C_{data}(t_i)$ are the measured values acquired during the N discrete time frames; N=34 for TAC$_1$ and N=35 for TAC$_2$. To avoid over-weighting short-duration early time frames, we used the weighting function $w_i = \delta t_i$ in Eq. 6, where $\delta t_i$ was the duration of the i-th time frame (because the t=2 hrs time-point in TAC$_2$ did not represent a true one-hour time bin beyond the TAC$_1$ data set, we used $\delta t_{35} = \delta t_{34} = 5$ mins). Equation 6 can be minimized with $C_{model}(t_i)$ calculated using trapezoidal integration.

An important tissue transport quantity is the distribution volume:

$$v_d \equiv \frac{k_1}{k_2 + k_3}. \qquad (7)$$

It represents the volume fraction of an imaged ROI in which tracer initially fills; i.e., rapidly equilibrates in. Patlak's formula, $$TBR(t) = v_b + (1 - v_b) v_d + K_i (1 - v_b) \frac{\int_0^t d\tau C_{In}(\tau)}{C_{In}(t)}, \qquad (8)$$

for the tumour-to-blood ratio at time t was used to "correct" TBR for distribution volume effects:

$$TBR_{corrected}(t) \equiv \frac{TBR(t) - v_b(1 - v_d)}{v_d} \qquad (9)$$

$$= 1 + k_3(1-v_b)\frac{\int_0^t d\tau C_{In}(\tau)}{C_{In}(t)}$$

In Eq. (8), $K_i \equiv k_3 v_d$ is sometimes referred to as the "net trapping rate". $TBR_{corrected}$ represents the theoretical tumour-to-blood ratio that would have arisen had the distribution volume been unity. Correlations were analyzed between $k_3$, $v_d$, TBR, and $TBR_{corrected}$, where TBR was calculated as $$TBR(t) \equiv \frac{C_{data}(t)}{C_{In}(t)} \tag{10}$$

at both t=1 and 2 hrs. Pearson correlation coefficients were calculated to quantify correlations between voxel- and tumour-scale values of these quantities. Voxel-scale coefficients were calculated by fitting the above model to the individual TACs for each voxel, while tumour-scale values were obtained using the average TAC in each tumour.

Correlations were reported as the population average (over twenty tumours) of the intra-tumour voxel-scale r values ("voxel-scale") and as correlations between tumour-scale values ("tumour-scale").

Example Results

Correlations Between TBR and $k_3$

Comparing voxel-scale $k_3$ and TBR values in each tumour, weak correlations were found at one hour (average of voxel-scale r values=0.10) and at two hours (r value=0.01). Strong correlations were found between voxel-scale $k_3$ and $TBR_{corrected}$ at one hour (population average r value=0.80) and moderate correlations were found at two hours (r value=0.53). Although standard imaging protocols call for measurement of TBR at least two hours after tracer injection, transport coefficient ($v_b$, $k_1$, $k_2$, $k_3$) values obtained using the one- and two-hour data sets were equivalent to within fit errors to the compartment model. The reduction in correlations is thus a metric for co-registration errors between the one- and two-hour data sets, as well as the diminished validity of Eq. (8), which may be only a good approximation at times less than the equilibration time $1/k_{eq}$. Representative voxel-scale correlations are shown in FIGS. 4A, 4B, 4C, and 4D for one patient. FIG. 5 displays population averages of voxel-scale correlations using the two-hour data sets as well as the mean values of the corresponding quantities. Specifically, the correlation matrix 510 of Pearson correlation coefficients between the mean voxel-scale parameters across the twenty tumours studied using the two-hour data sets is shown. Population average values 520 of the corresponding voxel-scale coefficients are also shown. Standard deviation of mean values across patients are indicated in parentheses.

Figure 5:
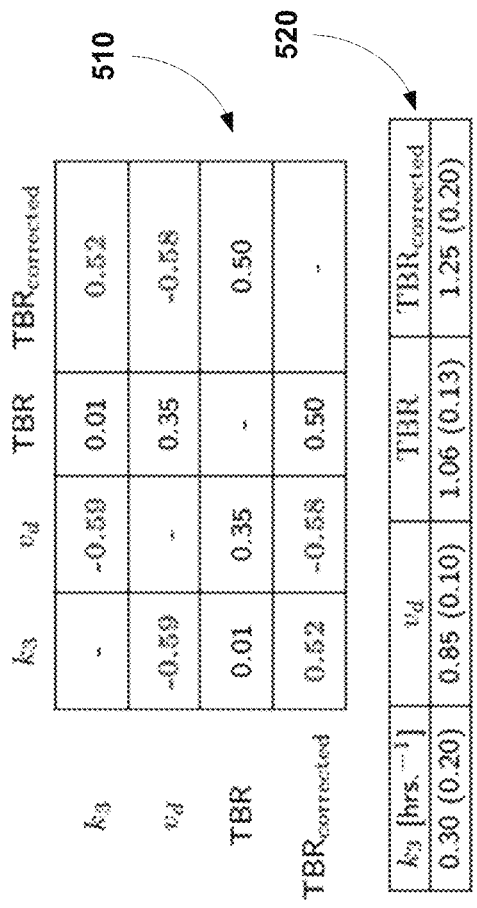
FIG. 5 depicts tables showing an example correlation matrix and example population average values of voxel-scale coefficients.
Figure 6:
FIG. 6 depicts a table showing an example correlation matrix between tumour-scale parameters.

Whole-tumour kinetics are less sensitive to co-registration errors and tumour-scale trapping rate exhibited modest correlations with TBR (across twenty patients, mean r=0.58) but strong correlations with $TBR_{corrected}$ (mean r=0.93); see FIGS. 4(E), (F) and FIG. 6. Mean tumour-scale values were identical to the values shown in FIG. 5 to within a few percent. FIG. 6 shows a correlation matrix 600 of Pearson correlation coefficients between the tumour-scale parameters across the twenty tumours studied using the two-hour data sets.

Relationship Between $v_d$ and $k_3$

Figure 8:
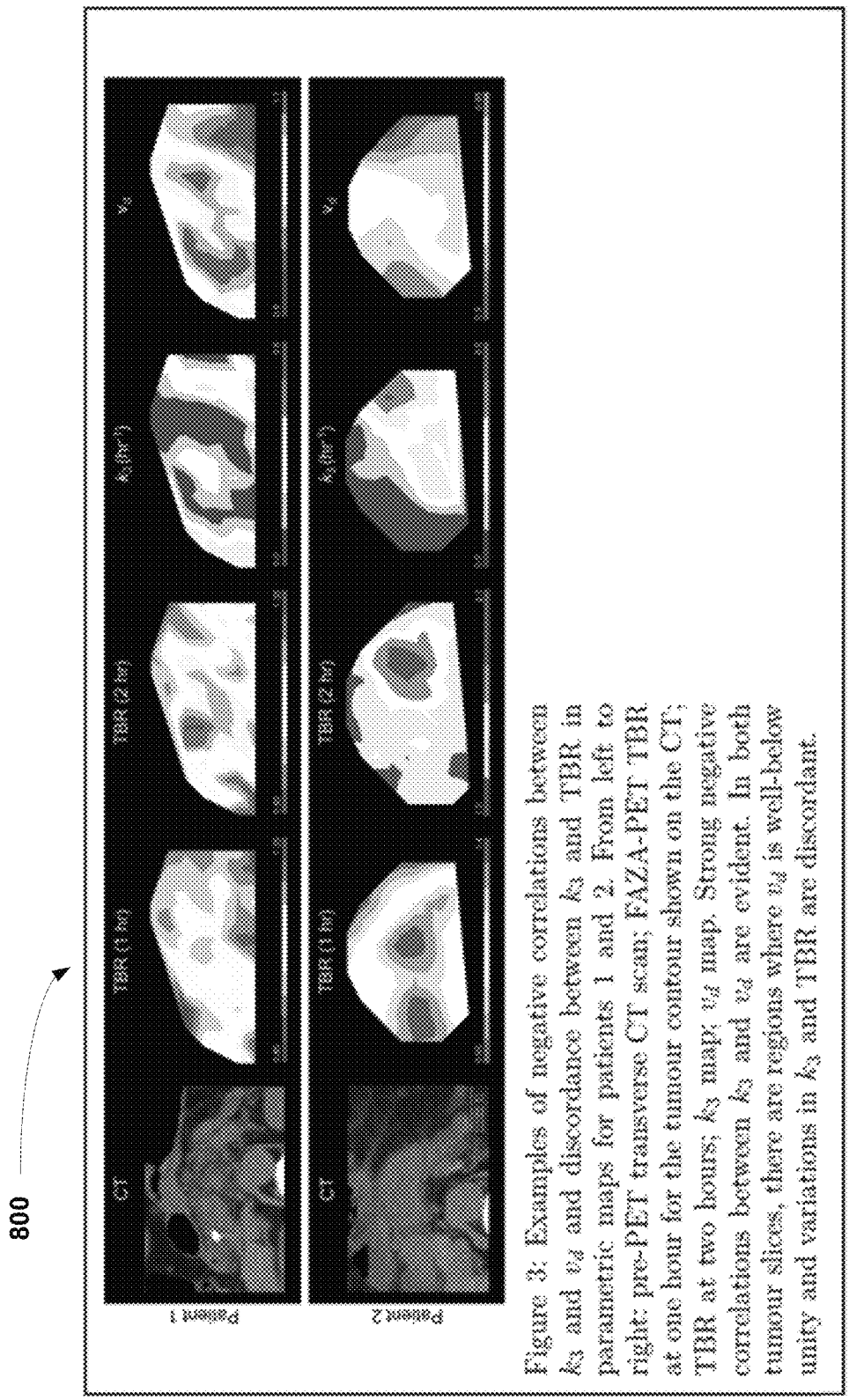
FIG. 8 depicts example images of tissue and example parametric maps.

In all patients, voxel-scale $k_3$ values were found to depend strongly on $v_d$ (population average of voxel-scale r-values=−0.59; see FIG. 5), with $k_3$ increasing as $v_d$ decreases. FIGS. 2(a.) and (d.) show two representative examples. Parametric maps of a transverse slice in each of these patients are shown in FIG. 8. FIG. 8 shows examples of negative correlations between $k_3$ and $v_d$ and discordance between $k_3$ and TBR in parametric maps for patients 1 and 2. From left to right scans 800 are shown for: pre-PET transverse CT scan; FAZA-PET TBR at one hour for the tumour contour shown on the CT; TBR at two hours; $k_3$ map; $v_d$ map. Strong negative correlations between $k_3$ and $v_d$ are evident. In both tumour slices, there are regions where $v_d$ is well-below unity and variations in $k_3$ and TBR are discordant. Tumour-scale correlations between $v_d$ and $k_3$ are reduced (r=−0.34) but still substantial; see FIG. 6.

To account for the unexpected correlations between $k_3$ and $v_d$, a model (shown schematically in FIG. 23) may be used in which an imaged voxel is comprised of two tissue types: one in which tracer reaches diffusive equilibration rapidly (with concentration $C^{(r)}$), and one in which it reaches equilibrium slowly (with concentration $C^{(s)}$):

$$C_d(t) = v_s C_d^{(s)} + (1-v_s)C_d^{(r)}(t). \tag{11}$$

Here $v_s$ represents the voxel volume fraction in which tracer is slow to equilibrate. Tracer may equilibrate slowly in mucinous and necrotic tissue owing to the slow diffusivity and long diffusive distances, respectively.

Having defined the above sub-compartments, the distributed-parameter compartment model that describes the effects of having regions of slow-equilibration is $$\frac{dC_d^{(r)}(t)}{dt} = \frac{k_1}{1-v_s}\left[C_{In}(t) - C_d^{(r)}(t)\right] - \left(k_b + \frac{k_{eq}v_s}{1-v_s}\right)C_d^{(r)}(t) + \frac{k_{eq}v_s}{1-v_s}C_d^{(s)}(t), \tag{12}$$

$$\frac{dC_d^{(s)}(t)}{dt} = k_{eq}\left[C_d^{(r)}(t) - C_d^{(s)}(t)\right], \text{ and} \tag{13}$$

$$\frac{dC_b(t)}{dt} = k_b C_d^{(r)}(t). \tag{14}$$

The factors of $1-v_s$ and $v_s$ here ensure detailed balance amongst the compartments. $k_b$ is the binding rate due to hypoxia and $k_{eq}$ represents the equilibration rate in the regions of slow-equilibration. This may be on the order of $(0.1 \to 1)$ hr$^{-1}$ when equilibration is driven by diffusion; see Eq. (2). In Eq. (14), it has been assumed that tracer does not bind inside regions of slow-equilibration since, for example, necrotic cells and extracellular mucous deposits do not bind hypoxia-PET nitroimidazole tracers.

At times $k_1^{-1} \ll t \ll k_{eq}^{-1}$, after diffusive equilibration is achieved in the rapidly-equilibrating regions [$C_d^{(r)}(t) \simeq C_{In}(t)$] but not yet in the slow-equilibrating regions, the tissue-to-blood ratio is readily obtained by integrating Eqs. (12)-(14):

$$TBR(t) \simeq \tag{15}$$

$$v_b + (1-v_b)(1-v_s) + \left(k_b + \frac{k_{eq}v_s}{1-v_s}\right)(1-v_b)(1-v_s)\frac{\int_0^t d\tau C_d^{(r)}(\tau)}{C_{In}(t)}.$$

This result neglects back-flux from the slow-diffusion region, dropping the contribution arising from $C_d^{(s)}$ in Eq. (13). This is valid as long as $t < k_{eq}^{-1}$.

Since $C_d^{(r)} \to C_{In}(t)$ for $t \geq k_1^{-1}$, Eq. (15) is identical to the Patlak result Eq. (8), with $$v_s = 1 - v_d, \text{ and} \tag{16}$$

$$k_3 = k_b + \frac{k_{eq}(1-v_d)}{v_d} \equiv k_b + K_{eq}(v_d), \tag{17}$$

where we have defined $$K_{eq}(v_d) = k_{eq}(1-v_d)/v_d. \tag{18}$$

Equations (16) and (17) can show that the distribution volume $v_d$ defined in Eq. (7) is the volume fraction of tissue in which tracer rapidly equilibrates and that the standard two-tissue compartment model trapping rate in general represents the sum of the rate of binding due to hypoxia and the equilibration rate. In turn, this means that it is not possible to distinguish binding from equilibration from just the shape of the time-activity curves. These equations are also valid for non-binding MR and CT imaging contrast agents, wherein $k_b=0$. The determination of $k_{eq}$ via Equation (17) can provide useful histopathological information for these imaging modalities since $k_{eq}$ is sensitive to such information via Equation (2).

To distinguish $k_b$ and $K_{eq}$ in $k_3$, voxel-scale $k_3$ values were arranged into bins based on distribution volume values. Because there will always be a cohort of normoxic voxels in a tumour for which $k_b=0$ (unless the hypoxic fraction is unity, Poissonian statistics dictates as much), it is assumed that the lowest M values of $k_3$ in these bins represent equilibration:

$$K_{eq}[(v_d)_i] = \frac{1}{M} \sum_{j=1}^{M} \min\left[\{k_3\}_{(v_d)_i}\right]_j. \tag{19}$$

Equation (19) is strictly valid in the limit where the variance in $k_{eq}$ values is much smaller than the variance in $k_b$ values (so that the two distributions can be distinguished). The choice of M is dictated by their relative sizes:

$$\frac{M}{N_b} = \frac{(\sigma_{k_{eq}}/k_{eq})}{\sqrt{(\sigma_{k_{eq}}/k_{eq})^2 + (\sigma_{k_b}/k_b)^2}}, \tag{20}$$

where $N_b$ is the total number of values within each bin, $\sigma$ x and X denote the standard deviation and mean values of X=$k_b$ or $k_{eq}$. Assuming that the relative variance ($(\sigma k_b/k_b)$ is equal to that for the oxygen partial pressure $P_{O2}$ (the case, e.g., when the two are related by a Michaelis-Menten-type relation), the variance in $k_b$ is expected to be large, based on the broad distribution of $P_{O2}$ levels in tumours: $((\sigma P_{O2}/P_{O2}) \leq 1$. In contrast, the relative variance in $k_{eq}$—reflecting that of the size l of the regions in which tracer is slow to equilibrate—is small. This was estimated by calculating the variance in the minimum $k_3$ value in each bin with respect to a $v_d$-dependent average (see e.g., the curve fits in FIG. 7 where dependence of the trapping rate on tracer equilibration and binding is shown. Graphs 7(a.) and (d.) show voxel-scale trapping rate values versus voxel-scale TBR values for patients 1 and 2, respectively. Graphs 7(b.) and (e.) show the corresponding equilibration rates, calculated from Eq. (19); the solid lines indicate fits to Eq. (18), yielding $k_{eq}=0.45$ hrs$^{-1}$ for patient 1 and $k_{eq}=0.52$ hrs$^{-1}$ for patient 2. Graphs 7(c.) and (f.) show the voxel-scale binding rates $k_b$ calculated from Eq. (17) using the $K_{eq}$ values shown in graphs 7(b.) and (e.)). Across our twenty patients, we found an average value ($\sigma k_{eq}/k_{eq}$)~0.4. As a compromise to having a sufficient number of voxels to ensure the validity of statistics and few enough to have sufficient resolution in $v_d$-space to carry out these curve fits, bins were chosen to contain ten voxels. Hence, we chose M=0.4×10=4. A sensitivity analysis of the predicted equilibration rates and the choice of M can be performed.

Figure 7:
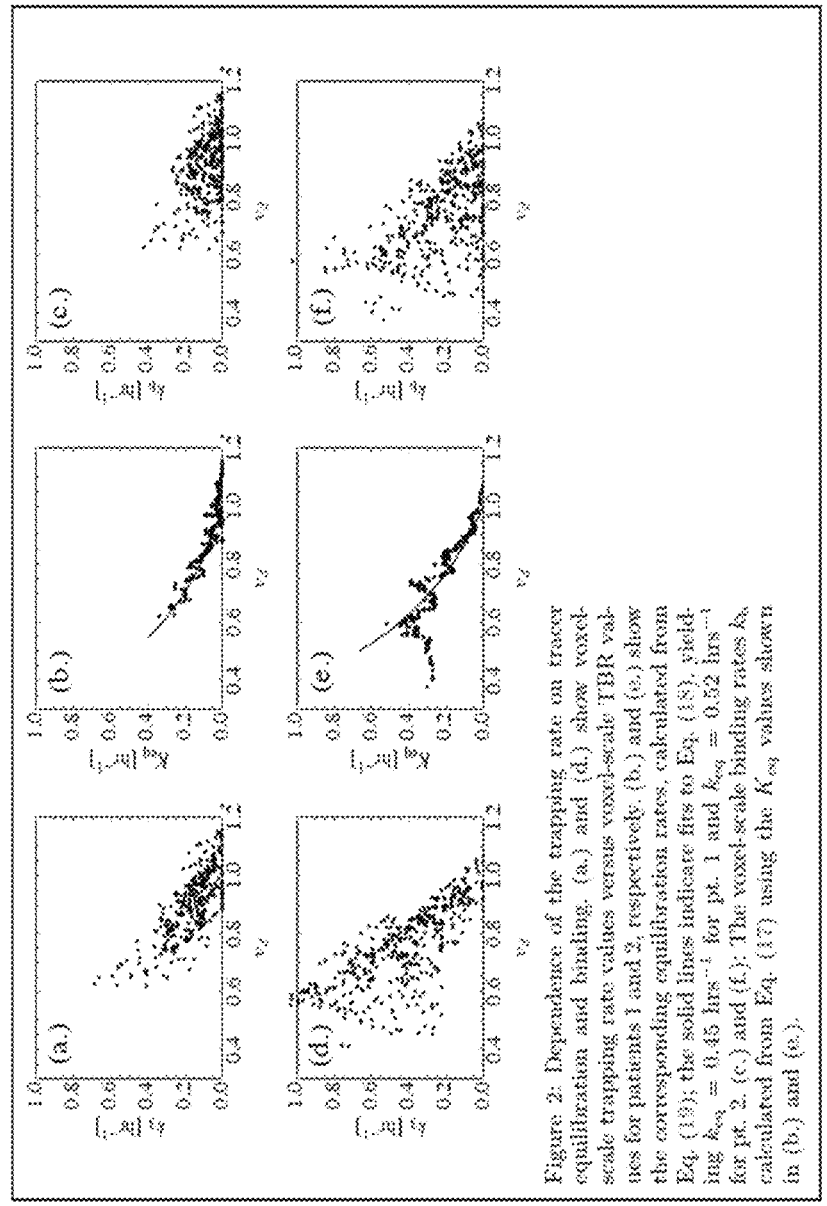
FIG. 7 depicts a set of graphs depicting example relationships between trapping rate and tracer equilibration and binding.
Figure 9:
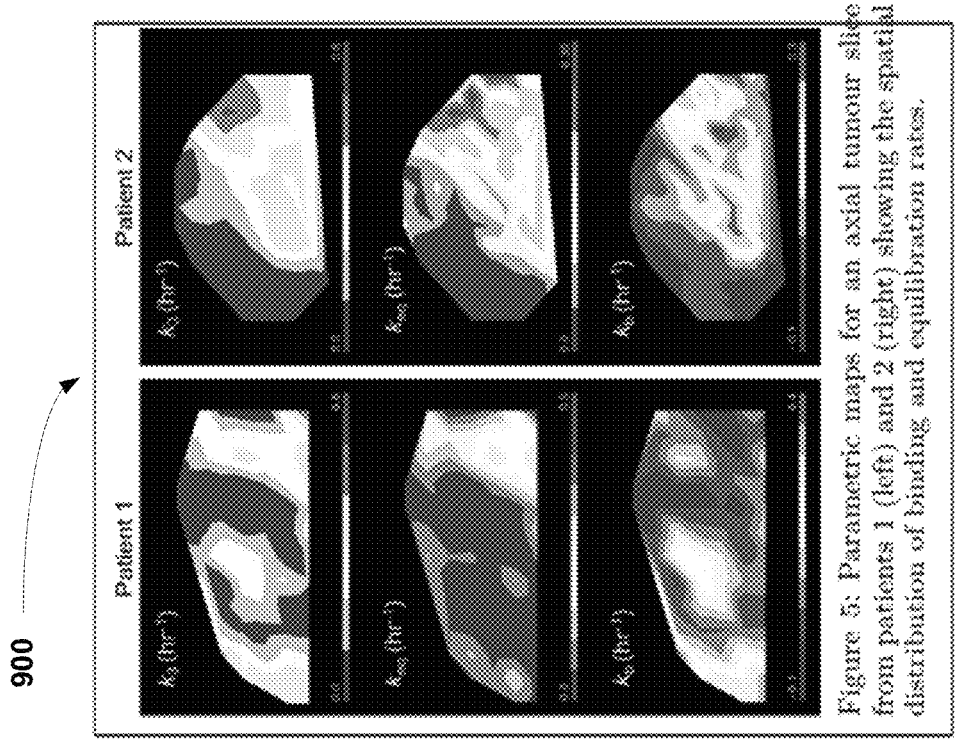
FIG. 9 depicts example parametric maps of tissue.

An example of this process is shown for two patients in FIGS. 7 and 9. Voxel-scale values of $K_{eq}$ in each of these bins as determined by Eq. (19) are plotted in FIGS. 7(B) and (E). The solid lines in these figures are fits to $K_{eq}(v_d)=k_{eq}(1-v_d)/v_d$. (The poor fit in FIG. 7(E) for $\lambda \leq 0.6$ may be due to a percolation effect: for distribution volumes less than ~0.65, regions of slow equilibration begin to overlap and $v_d$ will become dependent on the mean size l of these regions. Hence, from Eq. (2), $k_{eq}$ will also begin to depend on $v_d$.) Also shown in FIGS. 7(C) and (F) are the voxel-scale binding rates determined from Eqs. (17) and (19). FIG. 9 shows parametric maps of $k_3$, $k_{eq}$ and $k_b$ for the same tumour slices shown in FIG. 8. FIG. 9 shows parametric maps 900 for an axial tumour slice from patients 1 (left) and 2 (right) showing the spatial distribution of binding and equilibration rates.

Figure 10:
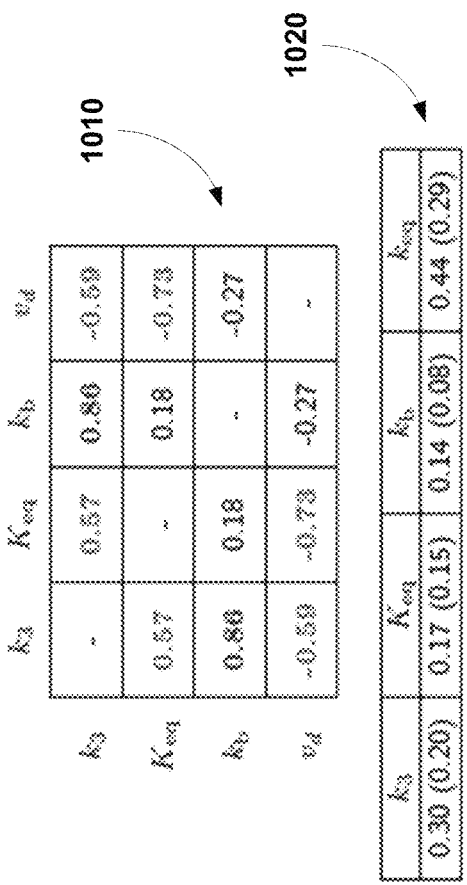
FIG. 10 depicts tables showing an example correlation matrix and example population average values of voxel-scale coefficients.

The correlation matrix 1010 between derived voxel-scale parameters from our model is shown in FIG. 10 along with population averages 1020 of these parameters. Correlation matrix 1010 of Pearson correlation coefficients between the mean voxel-scale parameters across the twenty tumours studied using the two-hour data sets. Population-averages 1020 of the corresponding voxel-scale rate coefficients are shown; values are shown in units of hrs$^{-1}$. Standard deviations of mean values across patients are indicated in parentheses. Also shown is the population average $k_{eq}$ value, which was calculated from fits to data from all voxels in each tumour. The relative sizes of the correlations between $k_3$ and $K_{eq}$ (r=0.57) and $k_b$ (r=0.86) are measures of how much equilibration and binding were found to contribute to the net trapping rate $k_3$. Most of the $v_d$ dependence of $k_3$ is contained in $K_{eq}$, as evidenced by the strong correlations between $v_d$ and $K_{eq}$ (r=−0.73) but comparatively weak correlations kb and $v_d$ (r=−0.27). Not shown are correlations between these quantities and the vascular influx rate $k_1$ since these were small (|r|<0.15) for all cases.

The $v_d$-dependence of $k_3$ in our model is a consequence only of mass conservation and the assumption that there exists a compartment in which tracer is slow to reach diffusive equilibrium. It does not depend on a specific microscopic model for equilibration. We tested the prediction given by Eq. (17) by fitting the binned $K_{eq}$ values to a function of the form $K_{eq}(v_d, \gamma)=k_{eq}[(1-v_d)/v_d] \gamma$ to determine how close was to its predicted value of unity. Averaging over all tumours, we found $\gamma=(0.9\pm0.4)$, with the error given by the standard deviation of values across all tumours. This confirms that our model in which tracer equilibrates slowly in a fraction $1-v_d$ of tissue is consistent with our data. The mean equilibration rate derived from these fits was $k_{eq}=0.44$ hrs$^{-1}$ (standard deviation of 0.29 hrs$^{-1}$ across all patients), corresponding to an equilibration time of $1/k_{eq}$~2.3 hrs.

The uptake of hypoxia-sensitive PET tracers is dependent on tissue transport properties as well as hypoxia. In principle, dynamic PET modeling corrects for transport properties such as slow tissue diffusivity that can impede the uptake of tracer and reduce sensitivity to hypoxia when such features are co-localized with hypoxia in PET voxels. This is especially problematic since PET voxels are typically large enough [~(4 mm)$^3$] to include diverse cell populations, with widely varying pathology. The quantity of primary interest in a compartment model analysis of dynamic PET imaging is the trapping rate $k_3$, believed to be sensitive to hypoxia via the underlying binding kinetics. Static PET imaging is more feasible clinically, however, and it is often assumed that one can adopt static imaging in place of kinetic imaging when some appropriate uptake metric—SUV for FDG-PET or TBR for hypoxia-PET—is well-correlated with $k_3$.

In an example experiment, dynamic and static PET were investigated in twenty patients with pancreatic adenocarcinoma (PDAC) and $k_3$ values were found to be only modestly correlated with TBR. A highly-variable distribution volume across patients was primarily responsible for the reduced correlations. This may be determined by processes using Patlak's formula. This may be consistent with FMISO kinetics in head and neck tumours.

Figure 4:
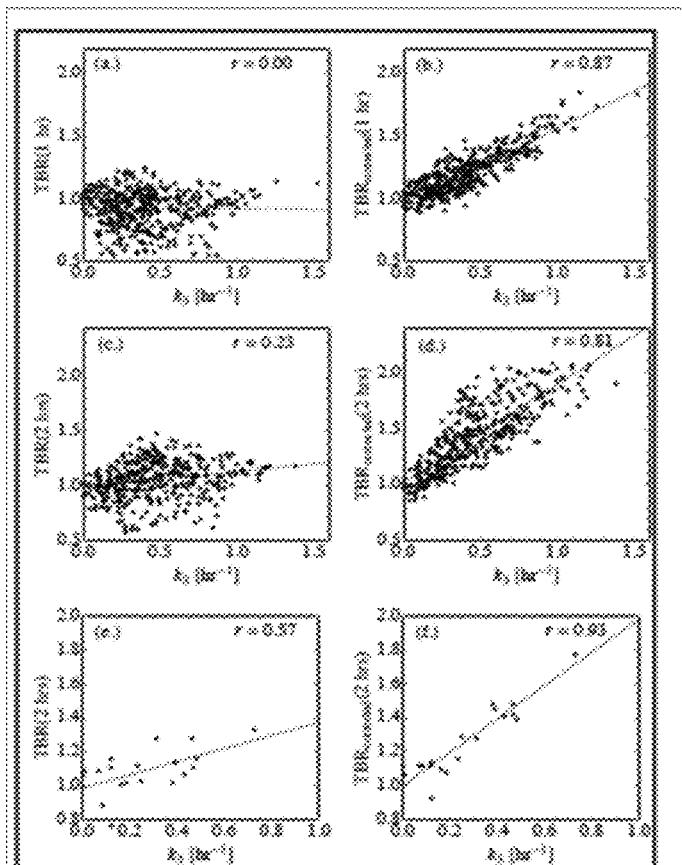
FIG. 4 is a set of graphs depicting example correlations between tumour-to-blood uptake ratios and trapping rates.
Figure 11:
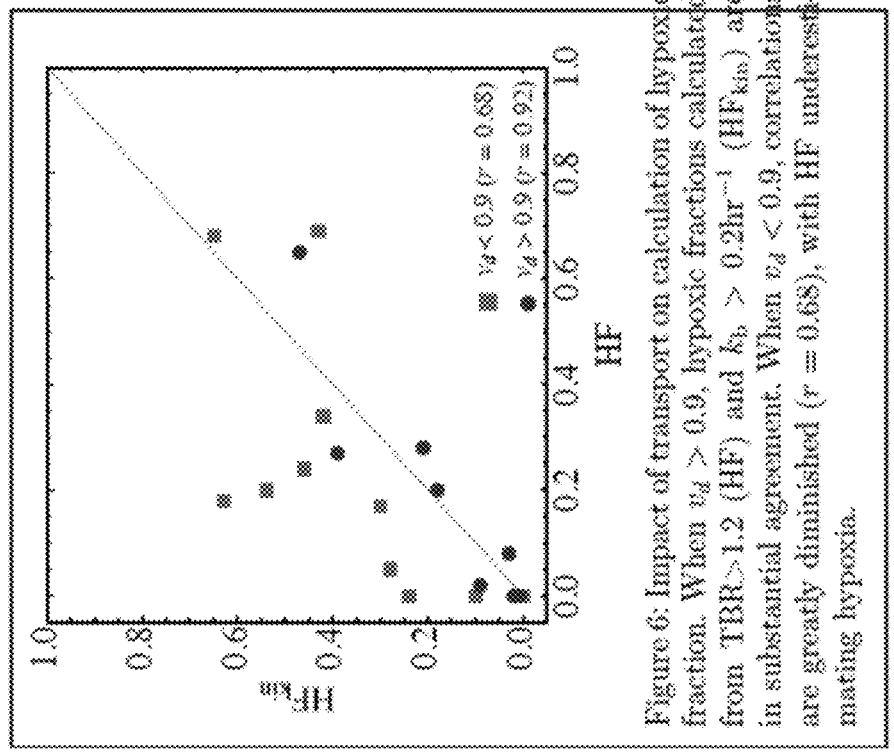
FIG. 11 depicts an example graph relating transport properties to hypoxic fraction.

Correcting for the distribution volume, correlations were considerably stronger and the corrected tumour-to-blood ratio was increased (see FIG. 4 that shows correlations between tumour-to-blood uptake ratios and the trapping rate are enhanced when uptake is corrected for the distribution volume. Graphs 400(a.), (c.) and (e.) show tumour-to-blood uptake ratio of FAZA versus trapping rate. Graphs 400(b.), (d.) and (f.) show tumour-to-blood uptake ratio corrected for the distribution volume versus trapping rate. Graphs 400(a.) and (b.) show voxel-scale values for a representative patient tumour (patient 2) using $TAC_1$. Graphs 400(c.) and (d.) voxel-scale values for a representative patient tumour (patient 2) using $TAC_2$. Graphs 400(e.) and (f.) show tumour-scale values using $TAC_2$ for all twenty tumours. Pearson correlation coefficients are shown.). This shows that tracer uptake at two hours in these patients is sensitive both to hypoxia and tissue transport properties (distribution volume), with the result that variability in tissue transport properties reduces the sensitivity of static PET imaging to hypoxia. FIG. 11 compares hypoxic fractions in the twenty tumours calculated using: a.) the fraction of voxels for which TBR>1.2 and b.) the fraction of voxels for which $k_b$>0.2 hr$^{-1}$, a threshold chosen such that the two hypoxic fractions agree when transport effects are small ($v_d$>0.9). When transport effects are substantial ($v_d$<0.9), correlations between the two methods of calculating hypoxic fractions are greatly reduced (r goes from 0.92 to 0.68), with the TBR approach underreporting hypoxia on average.

At first glance, this would suggest that these tumours would benefit from dynamic PET imaging. The trapping rate was found to exhibit a strong dependence on the distribution volume, however, implying that $k_3$ describes both the binding rate due to hypoxia as well as the rate of equilibration. A model was developed to explain this in which the extravascular tissue space was divided into two regions, one in which tracer rapidly achieved diffusive equilibration and one in which it equilibrated slowly. The population-averaged equilibration rate $k_{eq} \simeq =(0.44\pm0.29)$ hrs$^{-1}$ in the latter region is consistent with having either mucinous regions (on the order of tens to hundred of microns in extent) where diffusivity is greatly slowed or micronecroses, smaller than a PET imaging voxel but larger than ~500 μm across.

The long equilibration time [$1/k_{eq}$~2.3 hrs] implied by this result means that unbound tracer will not equilibrate until well-after tracer injection, at times t>>$1/k_{eq}$. At this time, the concentration of tracer in both the slow- and fast-equilibrating regions will approach that in blood and the effect of the distribution volume on TBR will vanish. Ideally, static hypoxia-PET imaging would be carried out when t>>$1/k_{eq}$ in order to remove this sensitivity to transport. Unfortunately, the half-life of $^{18}$F is short and imaging times are typically restricted to be three hours or less.

Figure 12:
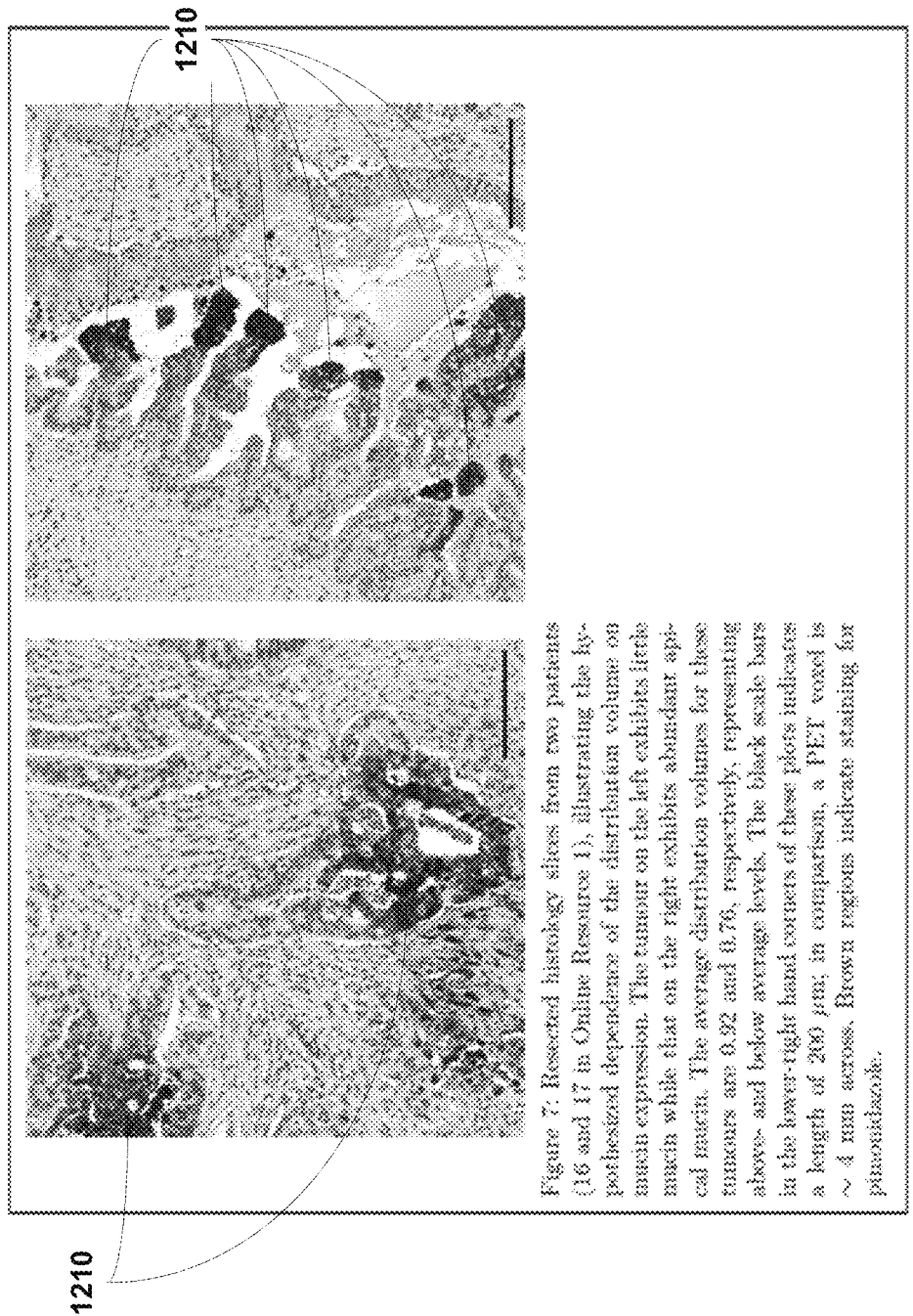
FIG. 12 depicts example resected histology slices.

If slow equilibration were due to necroses, $k_1$—a measure of perfusion—would be correlated with $k_{eq}$. No such correlations were found, suggesting that mucous deposits comprised the regions of slow equilibration. Necroses are also rare in PDAC, whereas mucous gel-forming mucins are commonly over-expressed. Amongst the twenty patients, the tumour volume fraction $v_d$ in which tracer equilibrated rapidly varied from 0.68 to 1, with an average value of 0.85. This implies mucinous region volume fractions ranging from 0 to 30%, with an average value of 15%. Tumours were resected in four patients and examined by a pathologist. Although not a sufficient number to be able to definitively attribute the reduced distribution volume to mucous, the patients with the smallest and largest distribution volumes of this four exhibited significant and negligible mucin expression, respectively; see FIG. 12. FIG. 12 shows resected histology slices from two patients, illustrating the hypothesized dependence of the distribution volume on mucin expression. The tumour on the left exhibits little mucin while that on the right exhibits abundant apical mucin. The average distribution volumes for these tumours are 0.92 and 0.76, respectively, representing above- and below average levels. The black scale bars in the lower-right hand corners of these plots indicates a length of 200 um; in comparison, a PET voxel is ~4 mm across. Some regions 1210 indicate staining for pimonidazole.

Our conclusion that equilibration is slow in parts of pancreatic tumours is not inconsistent with tumour-scale equilibration rates being rapid. The characteristic equilibration rate in the fast-equilibrating regions can be approximated by $k_1$ which, even for some hypo-perfused PDAC tumours, was fast compared to $k_b$ and $k_{eq}$. The population average of the tumour-scale $k_1$ values was ~0.3 min$^{-1}$. Regions of slow-equilibration occupy a relatively small fraction of the tumours and hence, the tumour-scale equilibration rate is not strongly affected by these.

The scheme described herein in example embodiments can differentiate binding from equilibration- and hence, quantify hypoxic status via the surrogate binding rate $k_b$. The accuracy may rely on the assumption that the variance in the equilibration rate is much smaller than the variance in the binding rate:

$$(\sigma_{k_{eq}}/k_{eq}) << (\sigma_{k_b}/k_b).$$

This allows attribution of the lowest few $k_3$ values in each $v_d$ bin to $K_{eq}$ and not $k_b$. Where the estimated ($\sigma$ $k_{eq}/k_{eq}$) is only marginally smaller than ($\sigma$ $k_b/k_b$) may suggest that equilibration and binding has not been completely distinguished. Hypoxic tissue quantification system 100 and data or models it is configured to generate in some embodiments represents an improvement over hypoxia quantification using $k_3$ since $k_3$ will always be larger than the $k_b$ generated by hypoxic tissue quantification system 100. Immunohistochemical staining of resected tumours can be used by hypoxic tissue quantification system 100 to generate data for comparison to data encoding estimates of $k_b$.

Beyond hypoxia quantification, dynamic PET imaging reveals additional information about tumour physiology that may prove to be clinically important. For example, in some embodiments, hypoxic tissue quantification platform 110 may facilitate determination of the distribution volume of FAZA (or other small-molecular weight imaging agents) and can be used to quantify the amount of mucous present in pancreatic tumours. Hypoxic tissue quantification platform 110 can be used to identify expression levels of mucin and stratify patients by prognosis and/or predict survival time, metastatic potential, and immune system avoidance. Overexpression of the mucous gel-forming mucin MUC5AC in PDAC is prognostic for shorter survival time, greater metastatic potential, and immune system avoidance. Hypoxic tissue quantification platform 110 can be used in relation to a variety of tissue types, for example, other tumour sites, to generate data indications of distribution volume, hypoxic status, and/or other complementary physiological information. Hypoxic tissue quantification platform 110 can be used by researchers or clinicians to understand activity (e.g., indicative of hypoxia) and related pharmacokinetic or physiological effects (e.g., distribution volume, binding rate) of molecules (e.g., hypoxia-sensitive tracers) in regions of interest (e.g., tumour tissue), uncovering and generating relationships between data captured from imaging such as PET scans. Hypoxic tissue quantification platform 110 can be used at a voxel- and/or whole tissue-scale.

Hypoxic tissue quantification platform 110 can be used with other hypoxia-PET tracers such as FMISO and in other tumour sites (e.g., head, neck). For example, hypoxic tissue quantification platform 110 may be used to determine $k_b$ or other features representing tissue transport effects to generate data indications reflecting a degree to which hypoxia quantification may be confounded by tissue transport effects. An impediment to tracer equilibration may be slow diffusivity. FAZA has been estimated to diffuse marginally faster than FMISO. In relation to other tracers, a variable distribution volume diminished correlations between TBR and $k_3$. (The fact that $K_i = v_d k_3$ but not $k_3$ was found to be well-correlated with TBR can be understood from Eq. (8): $K_i$ removes the variance in TBR arising from $v_d$ in the trapping term, but not the first two terms on the right-hand side of this equation.) The distribution volume may be important in static PET hypoxia quantification and significant negative correlations may exist between $k_3$ and $v_d$. In some embodiments, hypoxic tissue quantification platform 110 is configured to generate a novel model in which $k_3$ is sensitive both to hypoxia-induced binding as well as diffusive equilibration of unbound tracer and a novel biomarker of hypoxia, $k_b$. This can be used by hypoxic tissue quantification platform 110 to predict levels of hypoxic fractions in tissue, with clinical import for stratifying patients for hypoxia-targeted therapies where hypoxia, for example, in tumour tissue, correlates negatively with outcome.

The uptake of hypoxia-sensitive PET tracers in pancreatic tumours depends in a significant way on both tissue transport properties as well as the presence of hypoxia. Both dynamic- and static-PET based hypoxia surrogates—$k_3$ and TBR—are affected by regions where diffusive equilibrium is achieved very slowly, over several hours. In some embodiments, hypoxic tissue quantification platform 110 is configured to enable generation of a hypoxia-sensitive tracer binding rate from dynamic PET data and use same as a novel hypoxia biomarker. Hypoxic tissue quantification platform 110 can be used for a variety of applications, including all hypoxia-PET tracers and any tumour site where transport of small-molecular weight agents is challenged.

Hypoxia correlates negatively with outcome after surgery, radio- and chemo-therapies. There is a pressing need for reliable in vivo measurement scheme to stratify patients for hypoxia-targeted therapies.

Hypoxia-sensitive tracers are slow to bind in tumours. Uptake determined by hypoxia (low O2) and tissue transport (perfusion, local diffusion time). We correct for transport using compartment modelling of dynamic PET.

Compartment models+basic physics gives information beyond perfusion. Tissue transport: spatial distribution of necroses, regions of slow tracer diffusion: lipids, mucin, etc., for hypoxia-sensitive PET tracers such as FAZA as well as non-binding CT and MR imaging contrast agents.

The binding of nitromidazole analogues in hypoxic cells can be described as follows.

Figure 23:
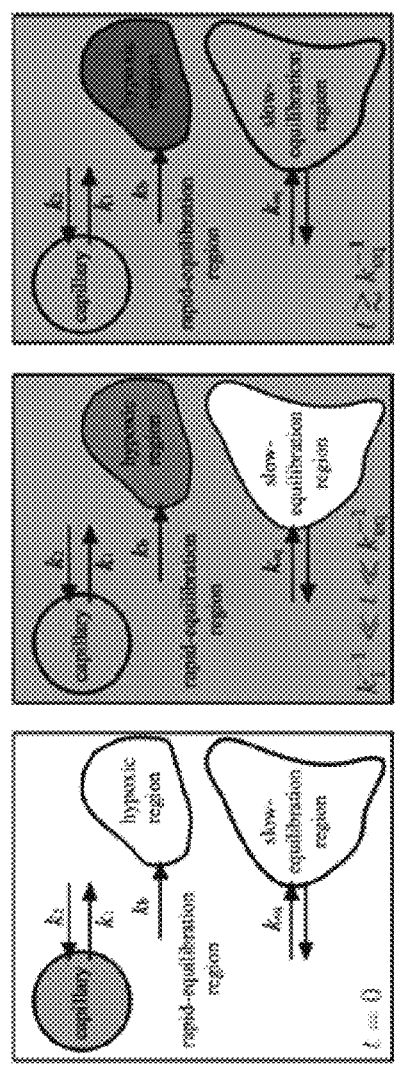
FIG. 23 depicts an example of a partitioning model.

As schematically shown in FIG. 23, hypoxia-sensitive tracers, such as FAZA, FMISO, etc., enter cells and bind to macromolecules in hypoxic regions (absence of O2). For these tracers as well as non-binding CT and MR imaging contrast agents, an additional kinetic parameter ($k_{eq}$) accounts for equilibration in regions where this process is slow.

PET voxel declared hypoxic if tumour-to-blood uptake ratio >1.2 at two hours. >20% increase due to hypoxia comparable to transport variances. In some embodiments, hypoxic tissue quantification platform 110 generates or uses compartment models of dynamic PET data to correct for transport.

Figure 13:
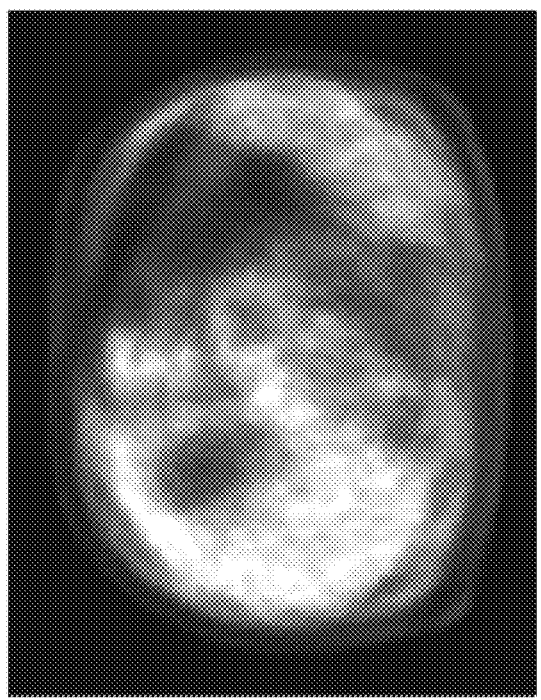
FIG. 13 depicts an example PET scan using FAZA.

FIG. 13 depicts an example PET scan using FAZA.

Figure 14:
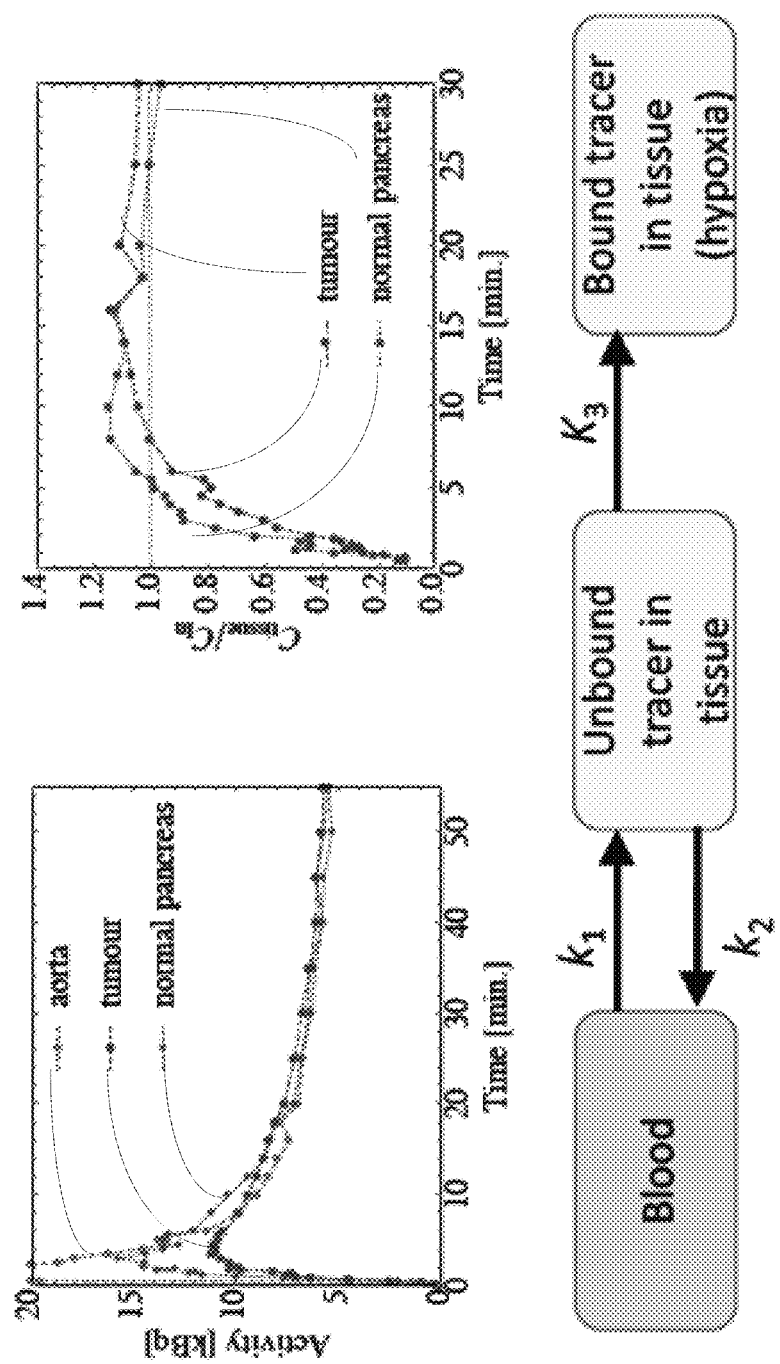
FIG. 14 depicts an example compartment model of FAZA dynamics.

FIG. 14 depicts a compartment model of FAZA dynamics. After initial equilibration period (5 to 10 min.), ratio of unbound FAZA in tissue and blood approaches a constant (distribution volume):

$$\left.\frac{C_d(t)}{C_{In}(t)}\right|_{t \gg k_1^{-1}} \to v_d \equiv \frac{k_1}{k_2 + K_3}$$

In an example experiment of an example embodiment, pancreatic tumours were "partitioned" ($v_d$ less than 1). In twenty patients with pancreatic ductal adenocarcinoma (PDAC), average tumour $v_d$=0.85, ranges from 0.7 to 1. This means that uptake of diffusing unbound FAZA varies by 0 to 30%. Major impact on hypoxia quantification from static PET measurements. Our explanation: nonequilibrium partitioning. No reason tumours should be substantially partitioned. Expect $v_d$=1.

Figure 15:
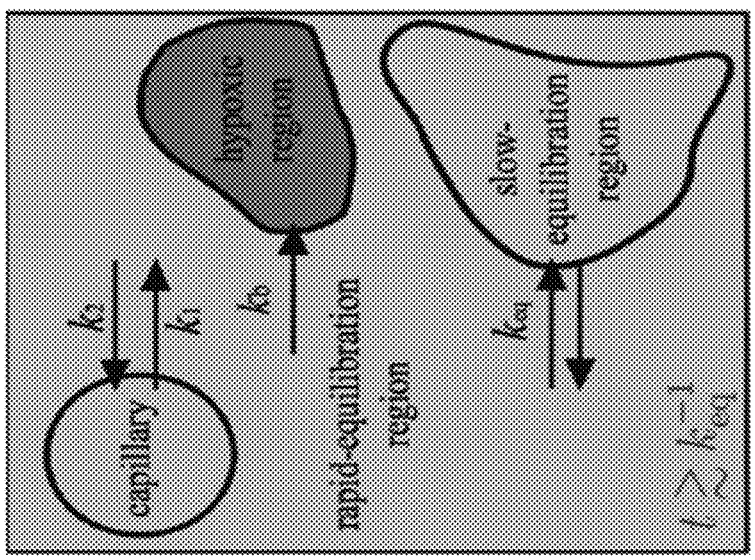
FIG. 15 depicts a representation of an example process of nonequilbrium partitioning (i.e., distribution volume less than one).
Figure 15:
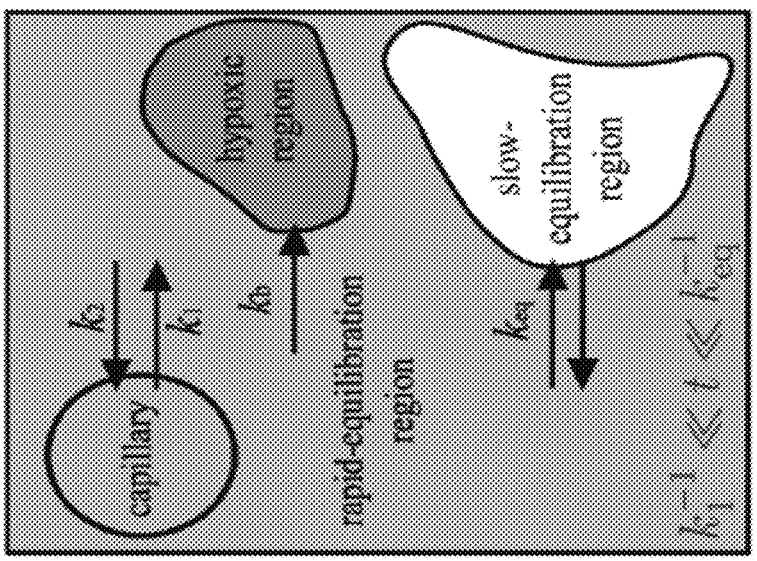
Figure 15:
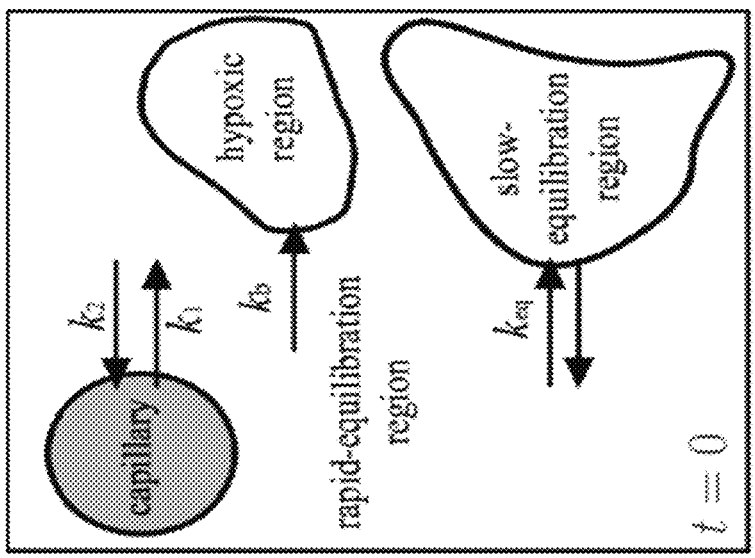

FIG. 15 depicts nonequilbrium partitioning. Nonequilibrium partition coefficient (equivalent to the distribution volume) is the ratio of concentrations of unbound tracer in the extravascular and vascular spaces a "short" time after injection.

Equilibration in partitioned regions is long, at times $$t \gg k_{eq}^{-1} \sim (1 \to 2) \text{ hrs}.$$

Figure 16:
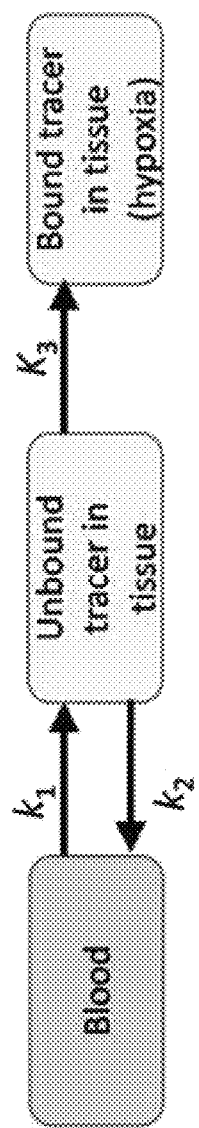
FIG. 16 depicts a schematic representation of a standard two-compartment model used to quantify hypoxia.

In some embodiments, hypoxic tissue quantification platform 110 generates a model for nonequilibrium partitioning. A schematic representation is depicted in FIG. 16.

Distribution volume is nonequilibrium value=excluded volume fraction of partitioned region:

$$v_d \equiv \frac{k_1}{k_2 + K_3} = 1 - v_s$$

Trapping rate is sum of binding and equilibration rate [see Equations (16) and (17)].

Figure 17:
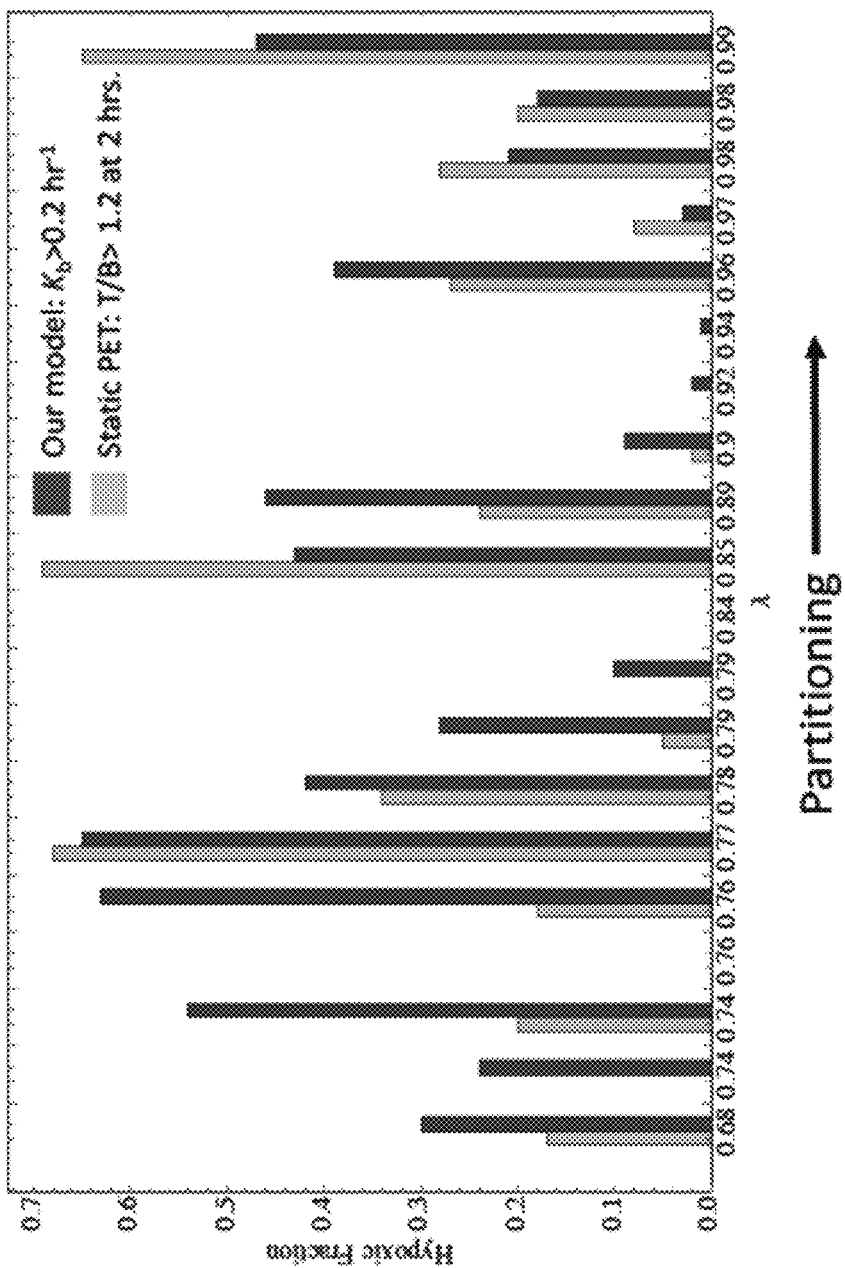
FIG. 17 depicts an example graph showing a relationship between hypoxic fraction and partitioning (equivalent to distribution volume).

FIG. 17 depicts a graph showing static PET underreports hypoxia when partitioning is significant.

Figure 18:
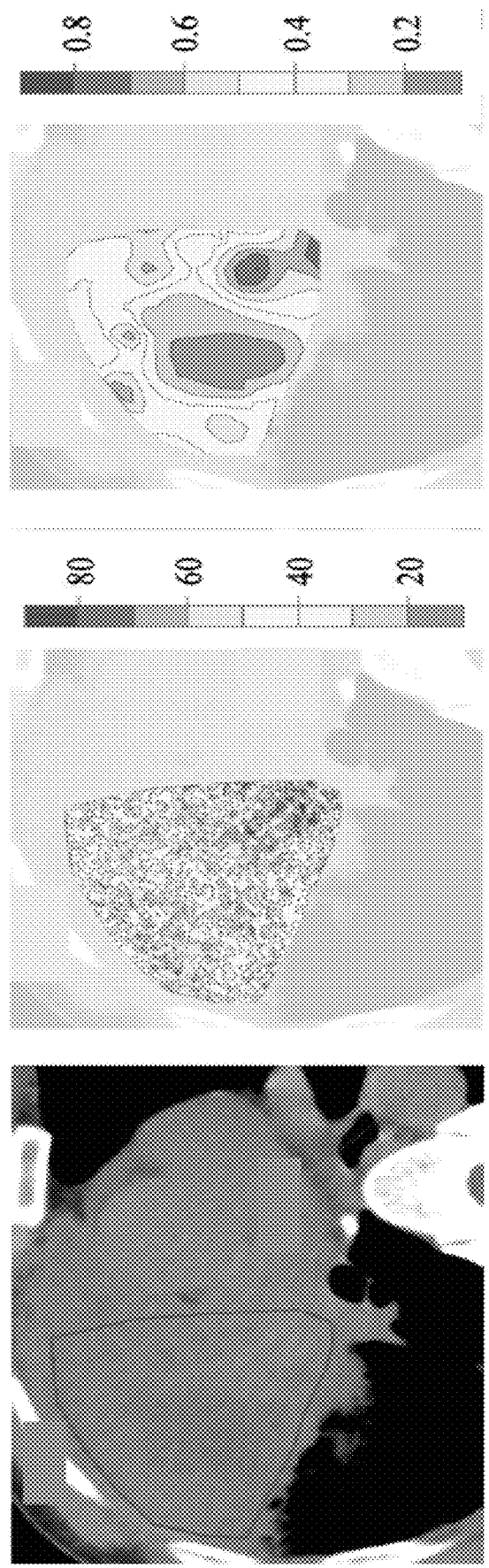
FIG. 18 depicts example images and graphs.
Figure 19:
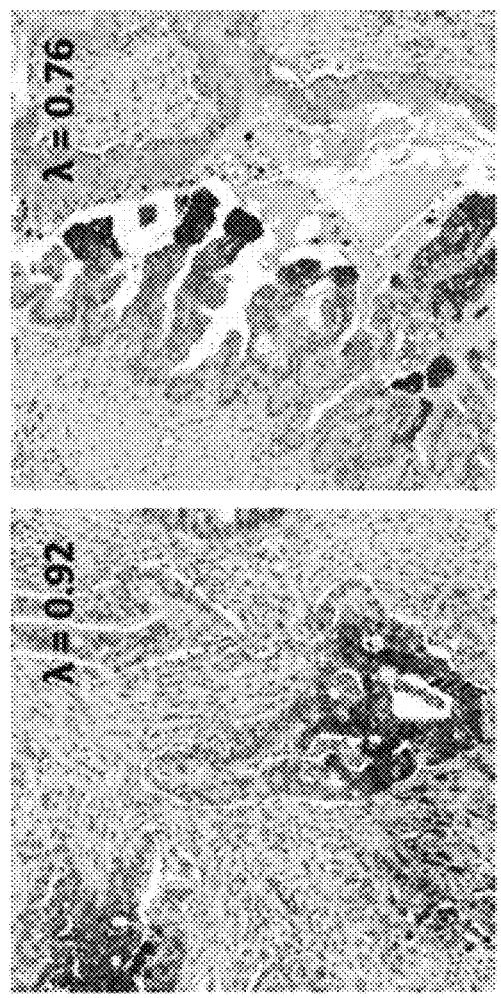
FIG. 19 depicts example stains.

As shown in FIG. 18, there can be a strong correlation between $v_d$ (equivalent to λ) and CT#: heavily partitioned regions are hypodense (watery). Partitioning can be due to mucin overexpression. This may be supported by pathology as shown in stains in FIG. 19.

Reliable quantification of hypoxia using PET is confounded by slow binding rate and (mucinous, necrotic, lipid-filled) regions that are slow to equilibrate.

Figure 20:
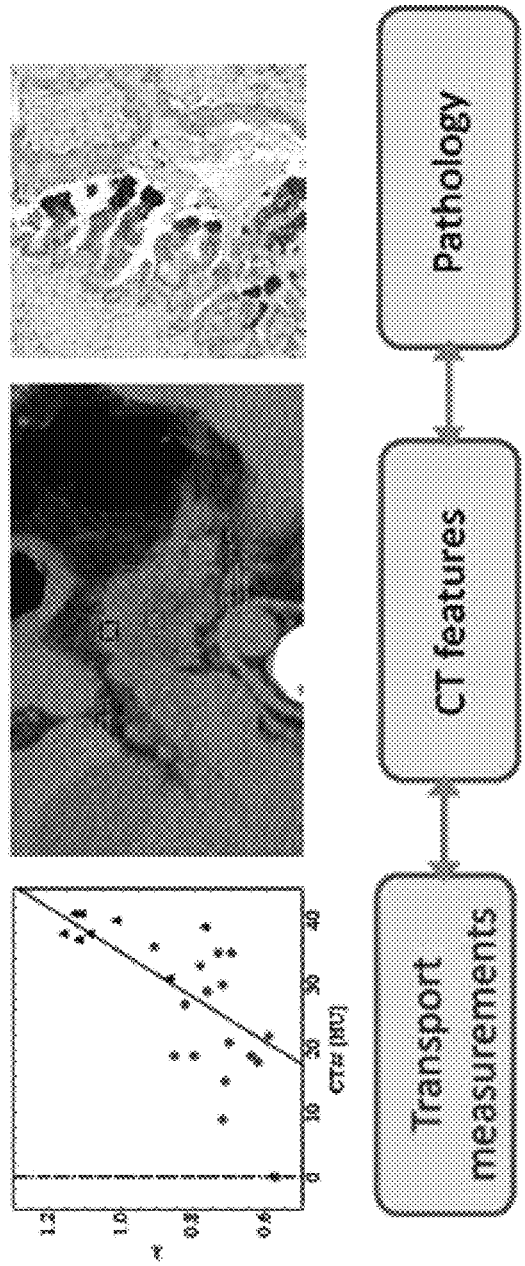
FIG. 20 depicts an example process of hypoxia tissue quantification system.

Compartment modelling of dynamic PET can enable uncovering more information than just perfusion. This can correct hypoxia-PET imaging and acquire (clinically relevant) information about tissue, as shown in FIG. 20.

Figure 21:
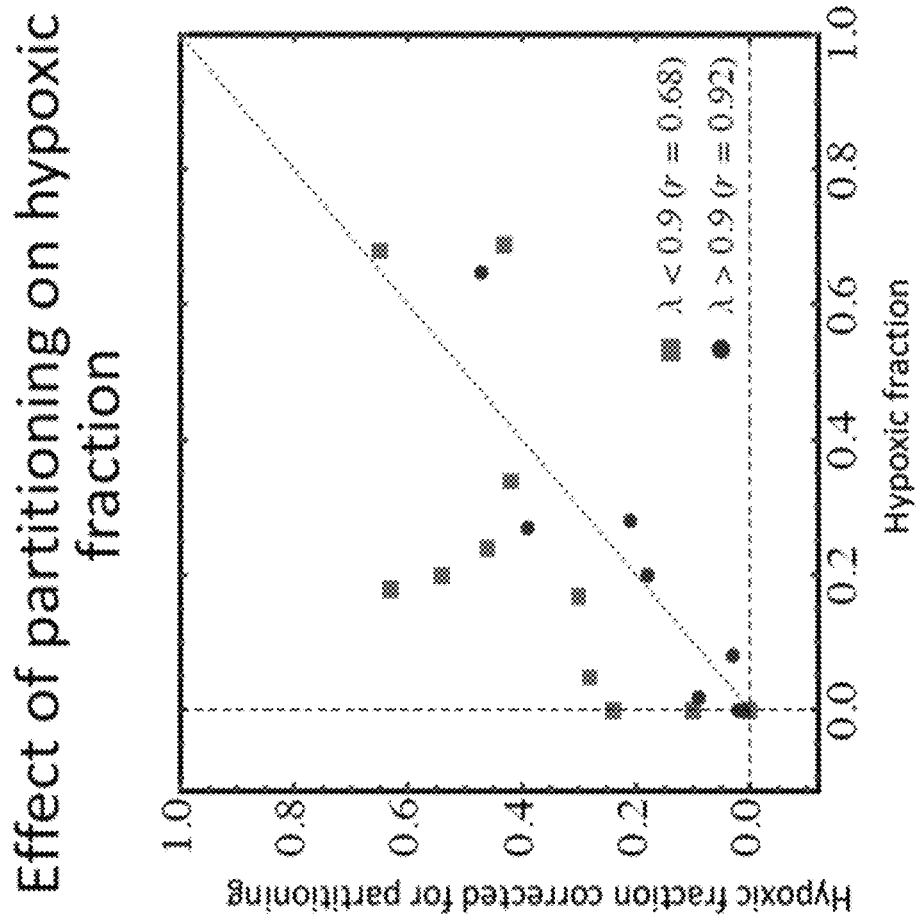
FIG. 21 depicts a graph showing an example effect of partitioning on hypoxic fraction.
Figure 22:
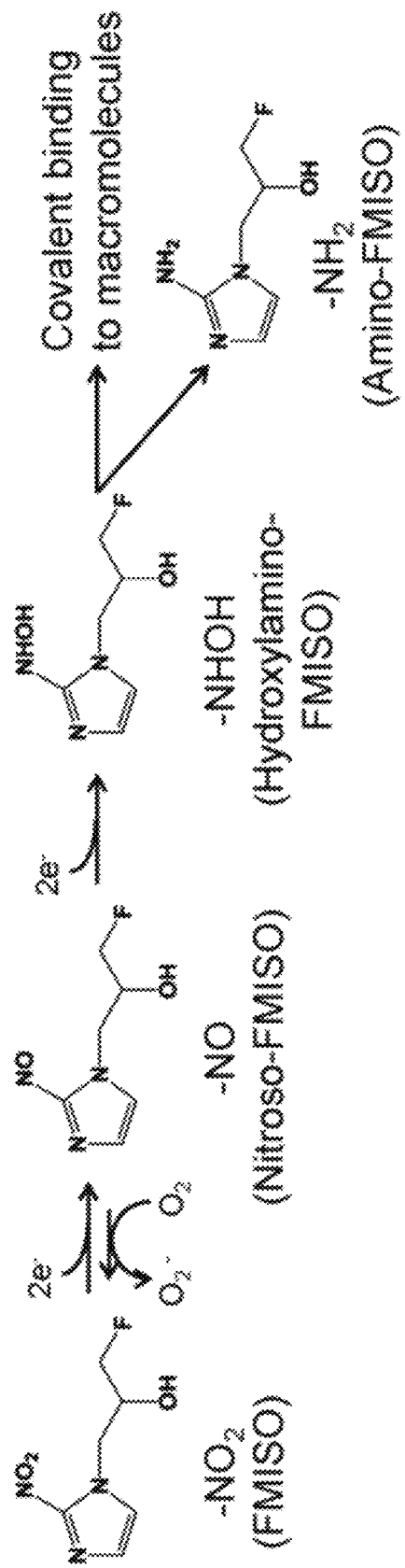
FIG. 22 depicts example binding of nitroimidazole analogues in hypoxic cells.

FIG. 21 depicts a graph showing the effect of partitioning on hypoxic fraction.

FIG. 24 is a schematic diagram of a computing device 2500 such as a server. As depicted, the computing device includes at least one processor 2502, memory 2504, at least one I/O interface 2506, and at least one network interface 2508.

Processor 2502 may be an Intel or AMD x86 or x64, PowerPC, ARM processor, or the like. Memory 2504 may include a suitable combination of computer memory that is located either internally or externally such as, for example, random-access memory (RAM), read-only memory (ROM), compact disc read-only memory (CDROM).

Each I/O interface 2506 enables computing device 2500 to interconnect with one or more input devices, such as a keyboard, mouse, camera, touch screen and a microphone, or with one or more output devices such as a display screen and a speaker.

Each network interface 2508 enables computing device 2500 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The foregoing discussion provides many example embodiments. Although each embodiment represents a single combination of inventive elements, other examples may include all possible combinations of the disclosed elements. Thus, if one embodiment comprises elements A, B, and C, and a second embodiment comprises elements B and D, other remaining combinations of A, B, C, or D, may also be used.

The term "connected" or "coupled to" may include both direct coupling (in which two elements that are coupled to each other contact each other) and indirect coupling (in which at least one additional element is located between the two elements).

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements. The embodiments described herein are directed to electronic machines and methods implemented by electronic machines adapted for processing and transforming electromagnetic signals which represent various types of information. The embodiments described herein pervasively and integrally relate to machines, and their uses; and the embodiments described herein have no meaning or practical applicability outside their use with computer hardware, machines, and various hardware components. Substituting the physical hardware particularly configured to implement various acts for non-physical hardware, using mental steps for example, may substantially affect the way the embodiments work. Such computer hardware limitations are clearly essential elements of the embodiments described herein, and they cannot be omitted or substituted for mental means without having a material effect on the operation and structure of the embodiments described herein. The computer hardware is essential to implement the various embodiments described herein and is not merely used to perform steps expeditiously and in an efficient manner.

For simplicity only one computing device 110 is shown in FIG. 2 but the respective systems may include more computing devices operable by users to access remote network resources and exchange data. The computing devices may be the same or different types of devices. The computing device includes at least one processor, a data storage device (including volatile memory or non-volatile memory or other data storage elements or a combination thereof), and at least one communication interface. The computing device components may be connected in various ways including directly coupled, indirectly coupled via a network, and distributed over a wide geographic area and connected via a network (which may be referred to as "cloud computing").

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

As can be understood, the examples described above and illustrated are intended to be exemplary only.

What is claimed is:

1. A method for generating output data indicating hypoxic fraction and equilibration kinetics of small molecular-weight imaging tracers using dynamic PET, CT, or MR imaging comprising, at a processor:
   processing dynamic PET, CT, or MR image data to extract an equilibration rate for a small molecular-weight imaging agent, wherein the dynamic PET, CT, or MR image data is kinetic PET, CT, or MR image data;
   processing dynamic PET image data to extract a hypoxia-sensitive tracer binding rate for a region of interest;
   generating the output data indicating hypoxic fraction and the equilibration rate for a small molecular-weight imaging agent using the hypoxia-sensitive tracer binding rate for the region of interest; and
   displaying visual elements representing the output data or making available the output data for further processing.

2. The method of claim 1 wherein the output data comprises parametric maps indicating a spatial distribution of binding and equilibrium rates.

3. The method of claim 1 wherein displaying the visual elements representing the output data comprises displaying the visual elements on a contoured image of the region of interest.

4. The method of claim 1 wherein the dynamic PET, CT, or MR image data is acquired over a time period, wherein the method further comprises generating PET activity data based on the dynamic PET acquired over the time duration, or MR or CT time concentration data based on the CT or MR image data is acquired over the time period.

5. The method of claim 1 wherein the dynamic PET, CT, or MR image data is acquired over a time period, wherein the method further comprises: processing the dynamic PET, CT, or MR image data based on time stamps for synchronization.

6. The method of claim 1 further comprising generating a compartment model, and fitting the compartment model to dynamic PET time-activity curves that correspond to the dynamic PET imaging data, or dynamic MR and CT time-concentration curves that correspond to the dynamic CT or MR image data.

7. The method of claim 6 wherein the compartment model involves the equilibration rate and the hypoxia-sensitive tracer binding rate.

8. The method of claim 1 further comprising receiving dynamic PET activity data for one or more regions of interest, generate data values encoding data points fitted to dynamic PET time activity curves, and generating data representations of relationships between features of the PET activity data for generation of the hypoxia-sensitive tracer binding rate.

9. The method of claim 1 further comprising storing or using a compartmental model to generate the hypoxia-sensitive tracer binding rate.

10. The method of claim 1 further comprising generating pharmacokinetic data from PET activity data.

11. A non-transitory computer-readable storage medium comprising computer-executable instructions for causing a processor to output data indicating hypoxic fraction and equilibration kinetics of small molecular-weight imaging tracers using dynamic PET, CT, or MR imaging by:
   processing dynamic PET, CT, or MR image data to extract an equilibration rate for a small molecular-weight imaging agent, wherein the dynamic PET, CT, or MR image data is kinetic PET, CT, or MR image data;
   processing dynamic PET image data to extract a hypoxia-sensitive tracer binding rate for a region of interest;
   generating the output data indicating hypoxic fraction and the equilibration rate for a small molecular-weight imaging agent using the hypoxia-sensitive tracer binding rate for the region of interest; and
   displaying visual elements representing the output data or making available the output data for further processing.

* * * * *